(12) United States Patent
Burger et al.

(10) Patent No.: US 9,573,969 B2
(45) Date of Patent: Feb. 21, 2017

(54) COMPOUNDS AND COMPOSITIONS AS KINASE INHIBITORS

(71) Applicants: Matthew T. Burger, Cambridge, MA (US); Savithri Ramurthy, Cambridge, MA (US); Benjamin R. Taft, Emeryville, CA (US)

(72) Inventors: Matthew T. Burger, Cambridge, MA (US); Savithri Ramurthy, Cambridge, MA (US); Benjamin R. Taft, Emeryville, CA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/851,249

(22) Filed: Sep. 11, 2015

(65) Prior Publication Data

US 2016/0075727 A1 Mar. 17, 2016

Related U.S. Application Data

(60) Provisional application No. 62/049,469, filed on Sep. 12, 2014.

(51) Int. Cl.

| | | |
|---|---|---|
| *C07D 213/74* | (2006.01) |
| *C07D 403/12* | (2006.01) |
| *C07D 413/04* | (2006.01) |
| *C07D 413/14* | (2006.01) |
| *C07F 9/6558* | (2006.01) |
| *A61K 31/675* | (2006.01) |

(52) U.S. Cl.
CPC ......... *C07F 9/65583* (2013.01); *A61K 31/675* (2013.01); *C07D 213/74* (2013.01); *C07D 403/12* (2013.01); *C07D 413/04* (2013.01); *C07D 413/14* (2013.01)

(58) Field of Classification Search
CPC ... C07D 213/74; C07D 403/12; C07D 413/04; C07D 413/14
See application file for complete search history.

(56) References Cited

U.S. PATENT DOCUMENTS

| | | | |
|---|---|---|---|
| 3,707,475 A | 12/1972 | Lombardino et al. |
| 5,717,100 A | 2/1998 | Selnick et al. |
| 6,211,177 B1 | 4/2001 | Sperl et al. |
| 6,248,771 B1 | 6/2001 | Shenoy et al. |
| 6,268,391 B1 | 7/2001 | Dickerson et al. |
| 6,358,932 B1 | 3/2002 | Monia |
| 6,399,603 B1 | 6/2002 | Jacobs et al. |
| 6,417,194 B1 | 7/2002 | Fox et al. |
| 6,458,813 B1 | 10/2002 | Mantlo et al. |
| 6,465,493 B1 | 10/2002 | Burgess et al. |
| 6,606,053 B2 | 8/2003 | Hayakawa et al. |
| 7,071,216 B2 | 7/2006 | Renhowe et al. |
| 7,423,150 B2 | 9/2008 | Costales et al. |
| 7,531,553 B2 | 5/2009 | Di Pietro et al. |
| 8,129,394 B2 | 3/2012 | Huang et al. |
| 8,242,260 B2 | 8/2012 | Costales et al. |
| 8,299,108 B2 | 10/2012 | Amiri et al. |
| 8,415,382 B2 | 4/2013 | Costales et al. |
| 8,563,553 B2 | 10/2013 | Costales et al. |
| 2001/0014679 A1 | 8/2001 | Tang et al. |
| 2003/0166633 A1 | 9/2003 | Gaster et al. |
| 2004/0053973 A1 | 3/2004 | Ohkawa et al. |
| 2004/0063946 A1 | 4/2004 | Ohkawa et al. |
| 2004/0087626 A1 | 5/2004 | Renhowe et al. |
| 2004/0122237 A1 | 6/2004 | Amiri et al. |
| 2005/0192287 A1 | 9/2005 | Costales et al. |
| 2005/0282805 A1 | 12/2005 | Hangeland et al. |
| 2009/0005359 A1 | 1/2009 | Cossrow et al. |
| 2009/0298815 A1 | 12/2009 | Adams et al. |
| 2013/0096149 A1 | 4/2013 | Madera et al. |
| 2013/0210818 A1 | 8/2013 | Huang et al. |
| 2013/0224195 A1 | 8/2013 | Costales et al. |
| 2014/0011825 A1 | 1/2014 | Costales et al. |
| 2014/0178360 A1 | 6/2014 | Kuo et al. |
| 2014/0275003 A1 | 9/2014 | Barsanti et al. |

FOREIGN PATENT DOCUMENTS

| | | |
|---|---|---|
| DE | 2155558 A1 | 6/1972 |
| DE | 3029376 A1 | 3/1982 |

(Continued)

OTHER PUBLICATIONS

Rautio et al., "Prodrugs: Design and Clinical Applications" Nature Review Drug Discovery 7:255-270, 2008.
Al-Ali et al., Chemical interrogation of the neuronal kinome using a primary cell-based screening assay. ACS Chem Biol. May 17, 2013;8(5)1027-36.
Andreyev et al., Kirsten ras mutations in patients with colorectal cancer: the multicenter "RASCAL" study. J Natl Cancer Inst. May 6, 1998;90(9):675-84.
Babchia et al., The PI3K/Akt and mTOR/P70S6K signaling pathways in human uveal melanoma cells: interaction with B-Raf/ERK. Invest Ophthalmol Vis Sci. Jan. 2010;51(1):421-9.
Banker, Modern Pharmaceutics. Marcel Dekker. New York. 1996. 3 pages.
Bos, Ras oncogenes in human cancer: a review. Cancer Res. Sep. 1, 1989;49(17):4682-9.
Brose et al., BRAF and RAS mutations in human lung cancer and melanoma. Cancer Res. Dec. 1, 2002;62(23):6997-7000.
Davies et al., Mutations of the BRAF gene in human cancer. Nature. Jun. 27, 2002;417(6892):949-54.

(Continued)

*Primary Examiner* — Rebecca Anderson
(74) *Attorney, Agent, or Firm* — Qian Zhang

(57) ABSTRACT

The present invention provides a compound of Formula I:

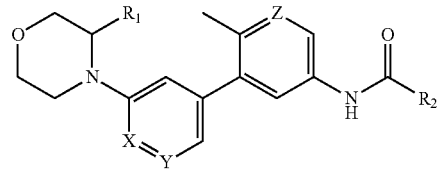

wherein X, Y, Z, $R_1$ and $R_2$ are as described herein, and salts thereof and therapeutic uses of these compounds for treatment of disorders associated with RAF kinase activity. The invention further provides pharmaceutical compositions comprising these compounds, and compositions comprising these compounds and a therapeutic co-agent.

8 Claims, No Drawings

(56) References Cited

FOREIGN PATENT DOCUMENTS

| | | |
|---|---|---|
| EP | 0149884 B1 | 12/1992 |
| EP | 1232153 B1 | 11/2004 |
| EP | 1721905 A1 | 11/2006 |
| GB | 2306108 A | 4/1997 |
| JP | 02-188579 A | 7/1990 |
| JP | 03-157383 A | 7/1991 |
| JP | 2000-302680 A2 | 1/2000 |
| JP | 2007-246520 A | 9/2007 |
| WO | 9808845 A1 | 3/1998 |
| WO | 0042012 A1 | 7/2000 |
| WO | 0059506 A1 | 10/2000 |
| WO | 0062778 A1 | 10/2000 |
| WO | 0138324 A2 | 5/2001 |
| WO | 0152845 A1 | 7/2001 |
| WO | 0152846 A1 | 7/2001 |
| WO | 0162756 A1 | 8/2001 |
| WO | 0166539 A1 | 9/2001 |
| WO | 0166540 A1 | 9/2001 |
| WO | 0172737 A1 | 10/2001 |
| WO | 01/96308 A1 | 12/2001 |
| WO | 0239954 A2 | 5/2002 |
| WO | 0242273 A2 | 5/2002 |
| WO | 0244156 A2 | 6/2002 |
| WO | 02064136 A2 | 8/2002 |
| WO | 02076960 A1 | 10/2002 |
| WO | 02094808 A1 | 11/2002 |
| WO | 03047577 A2 | 6/2003 |
| WO | 03082272 A1 | 10/2003 |
| WO | 03087304 A2 | 10/2003 |
| WO | 2004002948 A1 | 1/2004 |
| WO | 2004026859 A1 | 4/2004 |
| WO | 2004026863 A1 | 4/2004 |
| WO | 2004078163 A2 | 9/2004 |
| WO | 2004085425 A1 | 10/2004 |
| WO | 2005034869 A2 | 4/2005 |
| WO | 2005047266 A1 | 5/2005 |
| WO | 2005103028 A1 | 11/2005 |
| WO | 2005105814 A1 | 11/2005 |
| WO | 2005116000 A1 | 12/2005 |
| WO | 2005123050 A2 | 12/2005 |
| WO | 2006005914 A1 | 1/2006 |
| WO | 2006005915 A1 | 1/2006 |
| WO | 2006005918 A1 | 1/2006 |
| WO | 2006026306 A1 | 3/2006 |
| WO | 2006038734 A1 | 4/2006 |
| WO | 2006044509 A2 | 4/2006 |
| WO | 2007118149 A2 | 10/2007 |
| WO | 2008071605 A2 | 6/2008 |
| WO | 2009001132 A1 | 12/2008 |
| WO | 2009003998 A2 | 1/2009 |
| WO | 2009006389 A2 | 1/2009 |
| WO | 2009007749 A2 | 1/2009 |
| WO | 2009012283 A1 | 1/2009 |
| WO | 2009014637 A2 | 1/2009 |
| WO | 2009030952 A2 | 3/2009 |
| WO | 2009032667 A1 | 3/2009 |
| WO | 2009047163 A1 | 4/2009 |
| WO | 2009106885 A1 | 9/2009 |
| WO | 2009115572 A2 | 9/2009 |
| WO | 2009137391 A2 | 11/2009 |
| WO | 2009152356 A2 | 12/2009 |
| WO | 2010010154 A1 | 1/2010 |
| WO | 2010048149 A2 | 4/2010 |
| WO | 2010071837 A1 | 6/2010 |
| WO | 2011026911 A1 | 3/2011 |
| WO | 2011059610 A1 | 5/2011 |
| WO | 2011081205 A1 | 7/2011 |
| WO | 2011139107 A2 | 11/2011 |
| WO | 2012034363 A1 | 3/2012 |
| WO | 2012109075 A1 | 8/2012 |
| WO | 2013022766 A1 | 2/2013 |
| WO | 2013033167 A1 | 3/2013 |
| WO | 2013041652 A1 | 3/2013 |
| WO | 2013164769 A1 | 11/2013 |
| WO | 2013171640 A1 | 11/2013 |
| WO | 2014008214 A1 | 1/2014 |
| WO | 2014058691 A1 | 4/2014 |
| WO | 2014151616 A1 | 9/2014 |

OTHER PUBLICATIONS

De Bono et al., Therapeutics targeting signal transduction for patients with colorectal carcinoma. Br Med Bull. 2002;64:227-54.

Gopalsamy et al., Hit to lead optimization of pyrazolo[1,5-a]pyrimidines as B-Raf kinase inhibitors. Bioorg & Med Chem Lett. Oct. 2009;19(24):6890-2.

Hatzivassiliou et al., RAF inhibitors prime wild-type RAF to activate the MAPK pathway and enhance growth. Nature. Mar. 18, 2010;464:431-5. (Includes Methods page and Supplementary Information).

Hoshino et al., Constitutive activation of the 41-/43-kDa mitogen-activated protein kinase signaling pathway in human tumors. Oncogene. Jan. 21, 1999;18(3):813-22.

Kawasaki et al., The second messenger phosphatidylinositol-5-phosphate facilitates antiviral innate mmune signaling. Cell Host & Microbe. Aug. 14, 2013;14(2):148-58.

Lambert et al., Targeting the PI3K and MAPK pathways to treat Kaposi's-sarcoma-associated herpes virus infection and pathogenesis. Expert Opin Ther Targets. May 2007;11(5):589-99.

Martin et al., Inhibition of PIKfyve by YM-201636 dysregulates autophagy and leads to apoptosisindependent neuronal cell death. PLoS One Mar. 2013;8(3):1-14.

Moore et al., Phase I study of the raf-1 kinase inhibitor BAY 43/9006 in patients with advanced refractory solid tumors. Proceedings of the American Society of Clinical Oncology. 2002;21. Abstract 1816. <http://www.asco.org/portal/site/ASCO/template.RAW/menuitem.34d60f5624ba07fd506fe . . . > Last accessed Dec. 3, 2008. 2 pages.

Patani et al., Bioisosterism: A Rational Approach in Drug Design. Chem Rev. Dec. 19, 1996,96(8):3147-3176.

Pollock et al., High frequency of BRAF mutations in nevi. Nat Genet. Jan. 2003;33(1):19-20.

Rowinsky et al., Ras protein farnesyltransferase: A strategic target for anticancer therapeutic development. J Clin Oncol. Nov. 1999;17(11):3631-52.

Scharovsky et al., Inhibition of ras oncogene: a novel approach to antineoplastic therapy. J Biomed Sci. Jul.-Aug. 2000;7(4):292-8.

Strumberg et al., Final results of a phase I pharmacokinetic and pharmacodynamic study of the raf kinase inhibitor BAY 43/9006 in patients with solid tumors. Proceedings of the American Society of clinical Oncology. 2002;21. Abstract 121. <http://www.asco.org/portal/site/ASCO/template.RAW/menuitem.34d60f5624ba07fd506fe . . . > Last accessed Dec. 3, 2008. 2 pages.

Wenglowsky et al., Pyrazolopyridine inhibitors of B-RafV600E. Part 4: Rational design and kinase selectivity profile of cell potent type II inhibitors. Bioorg Med Chem Lett. Oct. 1, 2012;22(19):6237-41.

Wolff, Burger's Medicinal Chemistry and Drug Discovery. 5th Edition. vol. 1: Principles and Practice. John Wiley & Sons. 1995:975.

Yuen et al., Similarity of the phenotypic patterns associated with BRAF and KRAS mutations in colorectal neoplasia. Cancer Res. Nov. 15, 2002;62(22):6451-5.

Zuccotto et al., Through the "Gatekeeper Door": Exploring the active kinase conformation. J Med Chem. Apr. 8, 2010;53(7):2681-94.

CAS Registry No. 730972-83-5, STN Entry Date Aug. 23, 2004.
CAS Registry No. 867157-50-4, STN Entry Date Nov. 10, 2005.

Deng et al., Knowledge-based design of target-focused libraries using protein-ligand interaction constraints. J Med Chem. Jan. 26, 2006;49(2):490-500.

Jensen, a note on the term "Chalcogen." Journal of Chemical Education, Sep. 1997;74(9):1063-4.

Kim et al., Synthesis and biological evaluation of 4(5)-(6-alkylpyridin-2-yl)imidazoles as transforming growth factor-beta type 1 receptor kinase inhibitors. J Med Chem. Jun. 28, 2007;50(13):3143-7. Epub Jun. 7, 2007.

(56) References Cited

OTHER PUBLICATIONS

Kim et al., Synthesis of heteroaryl substituted imidazole derivatives. Bull Korean Chem Soc. 2000;21(3):345-7.
Krayushkin et al., Photochromic dihetarylethenes 7, synthesis . . . Russian Chemical Bulletin. International Edition. Jan. 2001;50(1):116-21.
Revesz et al., SAR of 2,6-diamino-3,5-difluoropyridinyl substituted heterocycles as novel p38 MAP kinase inhibitors. Bioorg Med Chem Lett. Aug. 19, 2002;12(16):2109-12. PubMed PMID: 12127515.
Tsai et al., Discovery of a selective inhibitor of oncogenic B-Raf kinase with potent antimelanoma activity. Proc Natl Acad Sci U S A. Feb. 26, 2008;105(8):3041-6.
White et al., Chemiluminescence in liquid solutions: The chemiluminescence of lophine and its derivatives. Photochemistry and Photobioloby. 1965;4:1129-55.
Wolin et al., Dual binding site inhibitors of B-RAF kinase. Bioorganic & Medicinal Chemistry Letters. Apr. 2008;18:2825-9.
Pearce et al., Failure modes in anticancer drug discovery and development, Cancer Drug Design and Discovery Edited by Stephen Neidle, Chapter 18, pp. 424-435 (2008).
Johnson et al., Relationships between drug activity in NCI preclinical in vitro and in vivo models and early clinical trials, Br J Cancer. May 18, 2001;84(10):1424-31.
Simone, Oncology: Introduction, Cecil Textbook of Medicine, 20th Edition, vol. 1, pp. 1004-1010, 1996.
Gura, Systems for identifying new drugs are often faulty, Science. Nov. 7, 1997;278(5340):1041-2.
Lyne et al., Identification of amidoheteroaryls as potent inhibitors of mutant (V600E) B-Raf kinase with in vivo activity, Bioorg Med Chem Lett. Feb. 1, 2009;19(3):1026-9.

COMPOUNDS AND COMPOSITIONS AS KINASE INHIBITORS

FIELD OF THE INVENTION

The invention provides compounds that inhibit Raf kinases, and are accordingly useful for treating certain disorders associated with excessive Raf kinase activity, including cell proliferation disorders such as cancers. The invention further provides pharmaceutical compositions containing these compounds and methods of using these compounds to treat conditions including cancer.

BACKGROUND

Protein Kinases are involved in very complex signaling cascades that regulate most cellular functions, including cell survival and proliferation. These signaling pathways have been heavily studied, particularly in the context of disorders caused by dysregulated cellular function, such as cancer. The mitogen-activated protein kinase (MAPK) cascade has been studied extensively, for example, and kinases in this pathway (e.g., RAS, RAF, MEK, and ERK) have been exploited as target sites for drug discovery. Mutated B-Raf is found in a significant fraction of malignancies (over 30% of all tumors and 40% of melanomas), and several drug candidates that inhibit a common B-Raf mutant (V600E, an activating mutation found in many cancers, particularly in cutaneous malignant melanoma, thyroid cancer, colorectal cancer, and ovarian cancer) have been reported, including GDC-0879, PLX4032, and PLX4720, while other inhibitors targeting C-Raf or B-Raf (or both) include sorafenib, XL281 RAF265, and BAY43-9006. These examples demonstrate that compounds that inhibit B-Raf or C-Raf are useful to treat various cancers.

The MAPK signaling cascade includes RAS, Raf, MEK and ERK kinases, each of which is actually a group of related proteins. These proteins function collectively as a signal transduction cascade where the number of distinct kinases and their varying substrate specificities create a complex and highly branched pathway. Raf, for example, consists of monomers referred to as A-Raf, B-Raf, and C-Raf (also called Raf-1), each of which functions primarily as a dimer. The RAF complex includes heterodimers as well as homodimers of these three species, bringing the total number of dimeric species in the Raf group to six, with each of these having a number of sites where phosphorylation at serine, threonine or tyrosine can cause either activation or inhibition. Due to the complexity of the pathway and its regulation, it has been reported that inhibitors of B-Raf can cause paradoxical activation of the pathway, apparently due to conformational effects on the kinase domain of Raf that affect dimerization, membrane localization, and interaction with RAS-GTP. In particular, ATP-competitive inhibitors can exhibit opposing effects on the signaling pathway, as either inhibitors or activators, depending on the cellular context. As a result, B-Raf inhibitors effective against tumors having the activating B-Raf mutation V600E may not be as effective as expected in tumors having wild-type B-Raf or KRas mutations.

The present invention provides novel inhibitors of Raf kinases, including A-Raf, B-Raf and/or C-Raf, and use of these compounds to treat disorders associated with excessive or undesired levels of Raf activity, such as certain cancers. The compounds of the invention minimize undesired pathway activation effects, and thus can be more efficacious and more predictable in vivo than the B-Raf inhibitors that cause paradoxical pathway activation even when they have similar in vitro potency. The compounds of the invention bind in a DFG-out mode, making them type 2 inhibitors, which have been reported to be less prone to induce paradoxical activation. The compounds are suited for treatment of BRaf wild-type and KRas mutant tumors, as well as B-Raf V600E mutant tumors.

SUMMARY OF THE INVENTION

In one aspect, the invention provides a compound of Formula I:

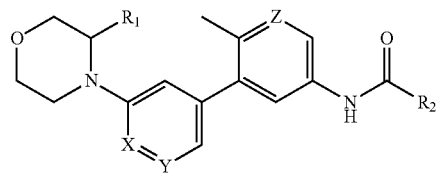

in which: $R_1$ is selected from hydrogen and methyl; $R_2$ is selected from pyridinyl and phenyl; wherein phenyl or pyridinyl can be substituted with a group selected from trifluoromethyl, 1,1-difluoroethyl and 2-fluoropropan-2-yl; X and Y are independently selected from N and C—OCH$_2$CHR$_3$R$_4$; wherein R$_3$ is selected from hydrogen and OH; and R$_4$ is selected from 2-(phosphonooxy)methyl and phosphonooxy; with the proviso that if X is N, Y is —C—OCH$_2$CHR$_3$R$_4$; and if Y is N, X is C—OCH$_2$CHR$_3$R$_4$; and Z is selected from N and CH.

In a second aspect, the present invention provides a pharmaceutical composition which contains a compound of Formula I or a N-oxide derivative, individual isomers and mixture of isomers thereof; or a pharmaceutically acceptable salt thereof, in admixture with one or more suitable excipients.

In another aspect, the compound of Formula I is an inhibitor of Raf kinases as shown by data herein, and is accordingly useful to treat conditions such as melanoma, breast cancer, sarcoma, GI tumors such as gastrointestinal stromal tumors, ovarian cancer, sarcoma, GI tumors such as gastrointestinal stromal tumors, and other malignancies associated with excessive Raf pathway activity, particularly in cancers driven by Ras mutations. In addition, the compound of the invention exhibits low levels of paradoxical activation of the Raf pathway.

In another aspect, the invention provides pharmaceutical compositions comprising a compound of Formula I admixed with at least one pharmaceutically acceptable carrier or excipient, optionally admixed with two or more pharmaceutically acceptable carriers or excipients.

In addition, the invention includes combinations of a compound of Formula I with a co-therapeutic agent, optionally including one or more pharmaceutically acceptable carriers, and methods of treatment using a compound of Formula I in combination with a co-therapeutic agent. Suitable co-therapeutic agents for use in the invention include, for example, cancer chemotherapeutics including but not limited to inhibitors of PI3K, other inhibitors of the Raf pathway, paclitaxel, docetaxel, temozolomide, platins, doxorubicins, vinblastins, cyclophosphamide, topotecan, gemcitabine, ifosfamide, etoposide, irinotecan, and the like.

In another aspect, the invention provides a method to treat a condition characterized by excessive or undesired levels of activity of Raf, especially B-Raf and/or C-Raf, which comprises administering to a subject in need of such treatment an effective amount of the compound of Formula I, or a pharmaceutical composition comprising such compound. The subject can be a mammal, and is preferably a human. Conditions treatable by the compound and methods described herein include various forms of cancer, such as solid tumors, melanoma, breast cancer, lung cancer (e.g., non-small cell lung cancer), sarcoma, GI tumors such as gastrointestinal stromal tumors, ovarian cancer, colorectal cancer, thyroid cancer, and pancreatic cancer. The invention thus includes the compound of Formula I, for use in therapy, particularly for use to treat cancers such as melanoma, breast cancer, lung cancer, liver cancer, sarcoma, GI tumors such as gastrointestinal stromal tumors, sarcoma, GI tumors such as gastrointestinal stromal tumors, ovarian cancer, colorectal cancer, thyroid cancer, and pancreatic cancer. The invention also includes use of such compounds for manufacture of a medicament for treating these conditions.

The invention includes the compound of Formula I and all stereoisomers (including diastereoisomers and enantiomers), tautomers and isotopically enriched versions thereof (including deuterium substitutions), as well as pharmaceutically acceptable salts of these compounds.

DETAILED DESCRIPTION

Description of Preferred Embodiments

The present invention provides a compound, compositions and methods for the treatment of kinase related disease, particularly Raf kinase related diseases; for example: various forms of cancer, such as solid tumors, melanoma, breast cancer, lung cancer (e.g., non-small cell lung cancer), sarcoma, GI tumors such as gastrointestinal stromal tumors, ovarian cancer, colorectal cancer, thyroid cancer, and pancreatic cancer.

In one embodiment, with respect to compounds of formula I, are compounds of formula Ia:

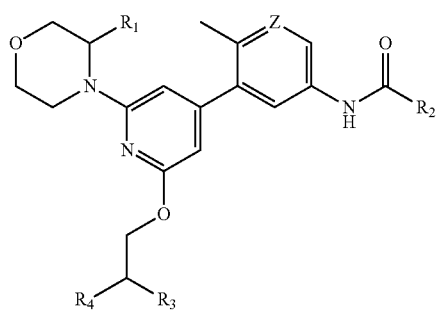

in which: $R_1$ is selected from hydrogen and methyl; $R_2$ is selected from pyridinyl and phenyl; wherein phenyl or pyridinyl can be substituted with a group selected from trifluoromethyl, 1,1-difluoroethyl and 2-fluoropropan-2-yl; $R_3$ is selected from hydrogen and OH; $R_4$ is selected from 2-(phosphonooxy)methyl and phosphonooxy; and Z is selected from N and CH; or a pharmaceutically acceptable salt thereof.

In a further embodiment is a compound, or a pharmaceutically acceptable salt thereof, selected from:

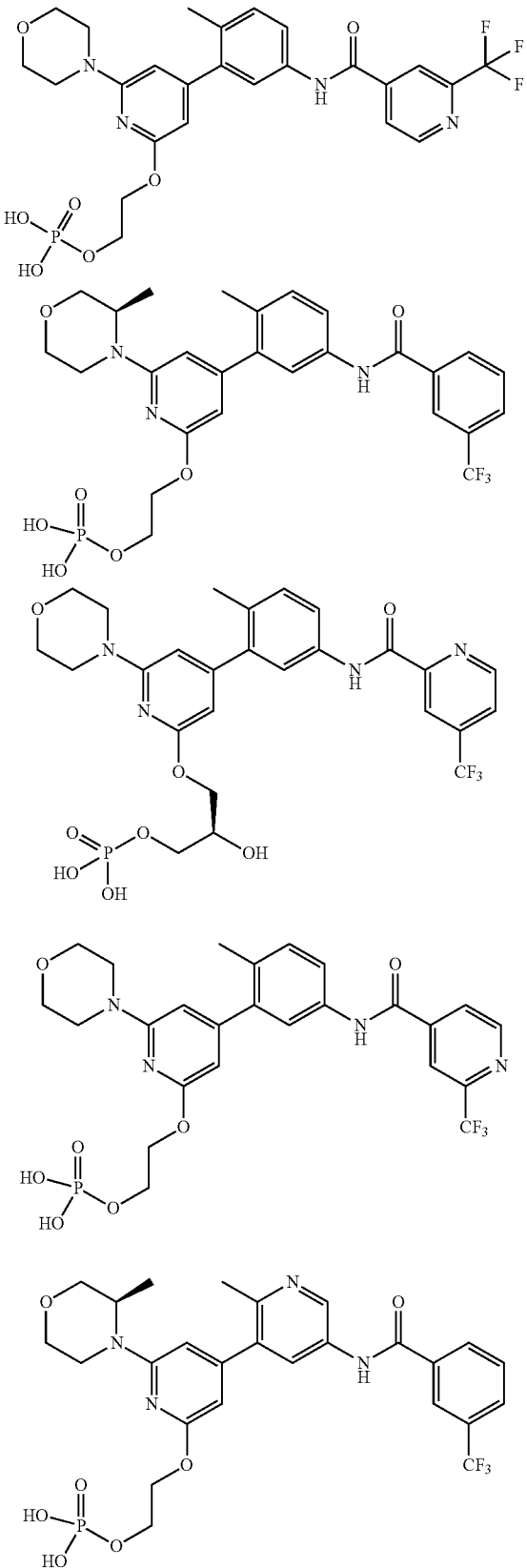

-continued

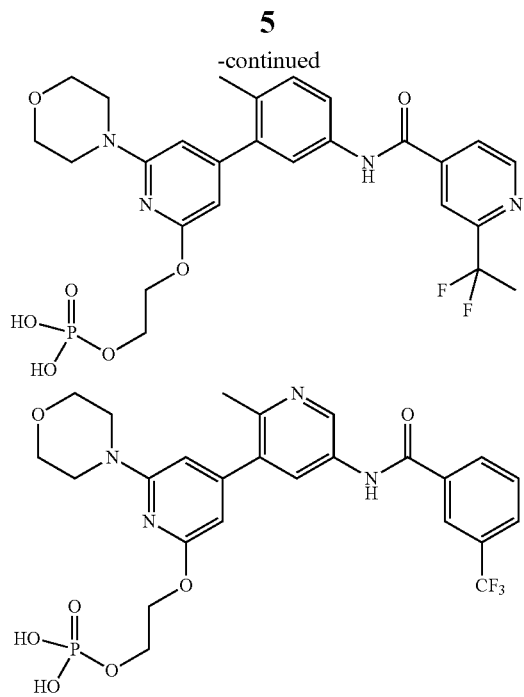

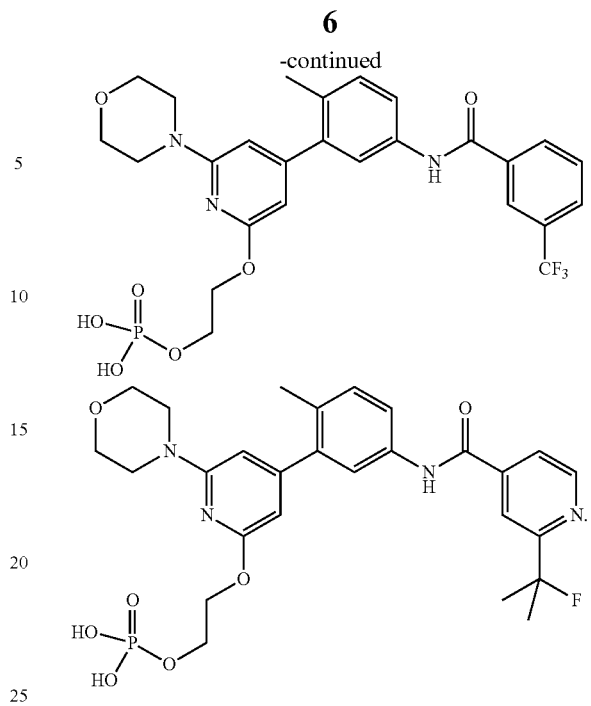

In another embodiment are compounds of formula Ib:

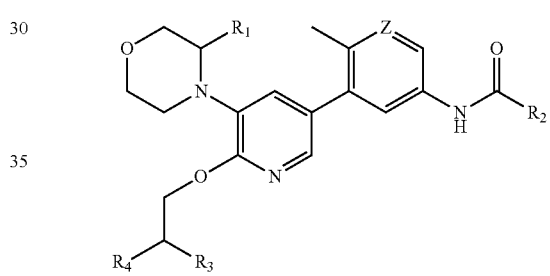

in which: $R_1$ is selected from hydrogen and methyl; $R_2$ is selected from pyridinyl and phenyl; wherein phenyl or pyridinyl can be substituted with a group selected from trifluoromethyl, 1,1-difluoroethyl and 2-fluoropropan-2-yl; $R_3$ is selected from hydrogen and OH; $R_4$ selected from 2-(phosphonooxy)methyl and phosphonooxy; and Z is selected from N and CH; or a pharmaceutically acceptable salt thereof.

In a further embodiment are compounds, or a pharmaceutically acceptable salt thereof, selected from:

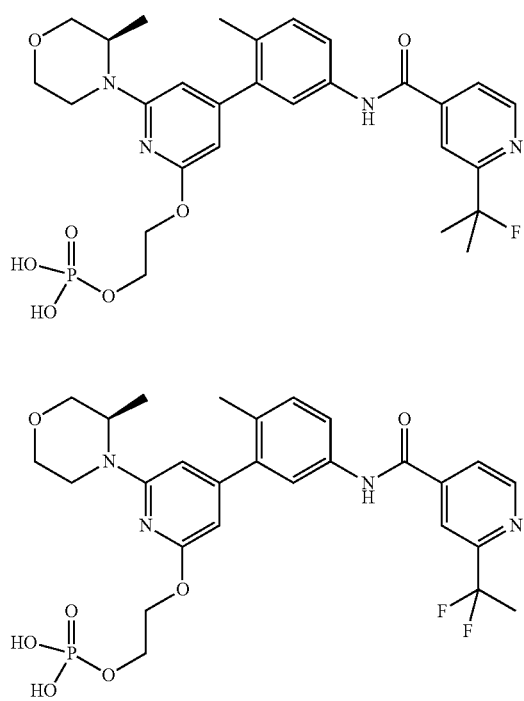

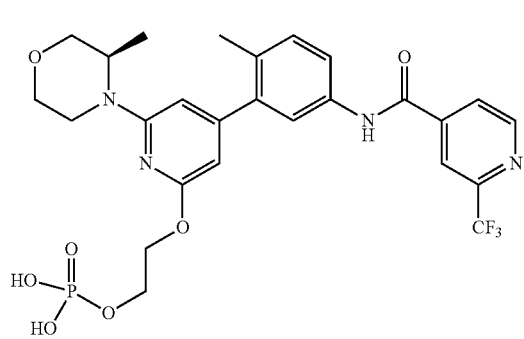

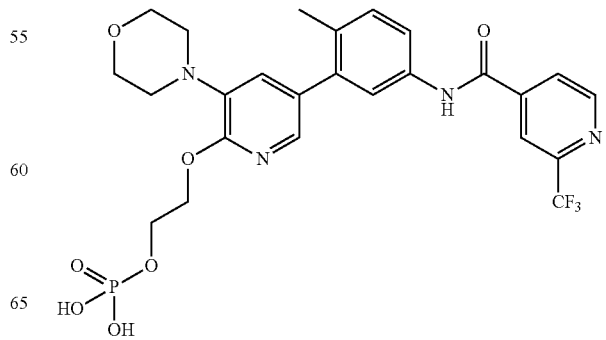

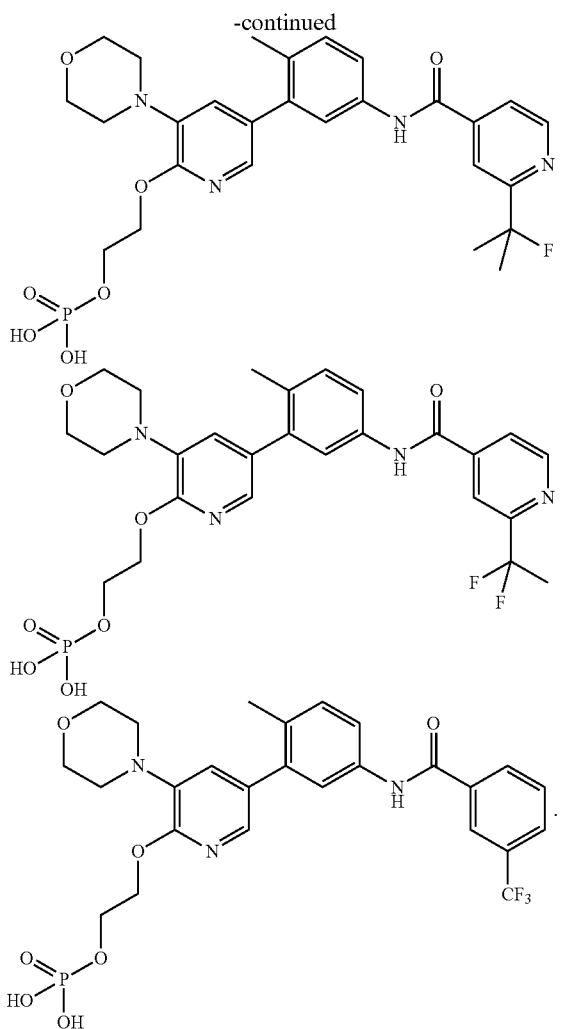

In another embodiment is a compound, or a pharmaceutically acceptable salt thereof, of formula:

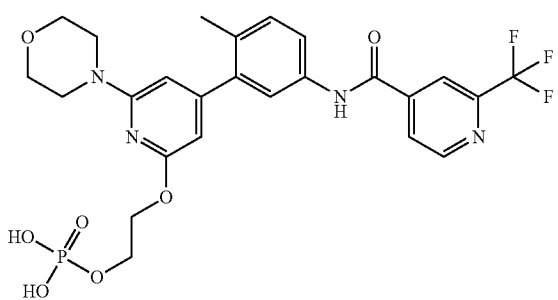 [SMILES: Cc1ccc(NC(=O)c2ccnc(C(F)(F)F)c2)cc1-c1cc(OCCOP(=O)(O)O)nc(N2CCOCC2)c1]

As used herein, the term "an optical isomer" or "a stereoisomer" refers to any of the various stereo isomeric configurations which may exist for the compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog 'R—S' system. When a compound is a pure enantiomer, the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and synthesis procedures, the compound can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration unless specified. If the compound contains a disubstituted cycloalkyl, the cycloalkyl substituent may have a cis- or trans-configuration, unless otherwise specified. All tautomeric forms are also intended to be included.

In many cases, the compound of the present invention is capable of forming acid and/or base salts by virtue of the presence of amino and/or carboxyl groups or groups similar thereto. As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlorotheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic or organic bases and can have inorganic or organic counterions.

Inorganic counterions for such base salts include, for example, ammonium salts and metals from columns I to XII of the periodic table. In certain embodiments, the counterion is selected from sodium, potassium, ammonium, alkylammonium having one to four C1-C4 alkyl groups, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Suitable organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, tetrahydrofuran, toluene, chloroform, dichloromethane, methanol, ethanol, isopropanol, or acetonitrile is desirable, where practicable.

Any formula given herein is also intended to represent unlabeled forms (i.e., compounds wherein all atoms are present at natural isotopic abundances and not isotopically enriched) as well as isotopically enriched or labeled forms of the compound. Isotopically enriched or labeled compounds have structures depicted by the formula given herein except that at least one atom of the compound is replaced by an atom having an atomic mass or mass number different from the atomic mass or the atomic mass distribution that occurs naturally. Examples of isotopes that can be incorporated into an enriched or labeled compound of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$, $^{31}P$, $^{32}F$, $^{35}S$, $^{36}Cl$, $^{125}I$ respectively. The invention includes various isotopically labeled compounds as defined herein, for example those in which radioactive isotopes, such as $^{3}H$ and $^{14}C$, or those in which non-radioactive isotopes, such as $^{2}H$ and $^{13}C$, are present at levels significantly above the natural abundance for these isotopes. These isotopically labeled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula I can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula I. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d^6$-acetone, $d^6$-DMSO, as well as solvates with non-enriched solvents.

Compounds of the invention, i.e. compounds of formula I that contain groups capable of acting as donors and/or acceptors for hydrogen bonds may be capable of forming co-crystals with suitable co-crystal formers. These co-crystals may be prepared from compounds of formula I by known co-crystal forming procedures. Such procedures include grinding, heating, co-subliming, co-melting, or contacting in solution compounds of formula I with the co-crystal former under crystallization conditions and isolating co-crystals thereby formed. Suitable co-crystal formers include those described in WO 2004/078163. Hence the invention further provides co-crystals comprising a compound of formula I.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease mediated by a Raf kinase such as B-Raf or C-Raf, or associated with activity of a kinase such as B-Raf or C-Raf, or (2) reduce or inhibit the activity of a kinase such as B-Raf or C-Raf in vivo.

In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of a kinase such as B-Raf or C-Raf, or at least partially reduce or alleviate a symptom or a condition associated with excessive Raf kinase activity.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In specific embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess of either the (R)- or (S)-configuration; i.e., for optically active compounds, it is often preferred to use one enantiomer to the substantial exclusion of the other enantiomer. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof. 'Substantially pure' or 'substantially free of other isomers' as used herein means the product contains less than 5%, and preferably less than 2%, of other isomers relative to the amount of the preferred isomer, by weight.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

In another aspect, the present invention provides a pharmaceutical composition comprising a compound of the present invention, or a pharmaceutically acceptable salt thereof, and at least one pharmaceutically acceptable carrier. The pharmaceutical composition can be formulated for particular routes of administration such as oral administration, parenteral administration, and rectal administration, and the like. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions for the compound of Formula I are tablets or gelatin capsules comprising an active ingredient of Formula I together with at least one of the following pharmaceutically acceptable excipients:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebulizer, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compound of formula I in free form or in salt form, exhibit valuable pharmacological activities, e g inhibiting the activity of A-Raf, B-Raf and/or C-Raf, as indicated by test data provided in the next sections, and is therefore indicated for therapy or for use as research chemicals, e.g. as tool compounds. The compound is especially useful for treatment of cancers driven by mutations in the Raf/Raf/MEK/ERK pathway, including cancers characterized by an activating Raf mutation such as Raf V600E, including but not limited to melanoma (e.g., malignant melanoma), breast cancer, lung cancer (e.g., non-small cell lung cancer), sarcoma, GI tumors such as gastrointestinal stromal tumors, ovarian cancer, colorectal cancer, thyroid cancer, and pancreatic cancer.

Thus, as a further embodiment, the present invention provides the use of a compound of formula I or any of the embodiments within the scope of Formula I as described herein, in therapy. In a further embodiment, the therapy is for a disease which may be treated by inhibition of A-Raf, B-Raf or C-Raf. In another embodiment, the compounds of the invention are useful to treat cancers, including but not limited to melanoma, breast cancer, lung cancer, sarcoma, GI tumors such as gastrointestinal stromal tumors, ovarian cancer, colorectal cancer, thyroid cancer, and pancreatic cancer.

In another embodiment, the invention provides a method of treating a disease which is treatable by inhibition of A-Raf, B-Raf or C-Raf, or a combination thereof, comprising administration of a therapeutically effective amount of a compound of formula I or any of the embodiments within the scope of Formula I as described herein. In a further embodiment, the disease is selected from the afore-mentioned list, suitably melanoma, breast cancer, lung cancer, sarcoma, GI tumors such as gastrointestinal stromal tumors, ovarian cancer, colorectal cancer, thyroid cancer, and pancreatic cancer. The method typically comprises administering an effective amount of a compound as described herein or a pharmaceutical composition comprising such compound to a subject in need of such treatment. The compound may be administered by any suitable method such as those described herein, and the administration may be repeated at intervals selected by a treating physician.

Thus, as a further embodiment, the present invention provides the use of a compound of formula I for the manufacture of a medicament. In a further embodiment, the medicament is for treatment of a disease which may be treated by inhibition of A-Raf, B-Raf or C-Raf. In another embodiment, the disease is a cancer, e.g., a cancer selected from the afore-mentioned list, including melanoma, breast cancer, lung cancer, sarcoma, GI tumors such as gastrointestinal stromal tumors, ovarian cancer, colorectal cancer, thyroid cancer, and pancreatic cancer.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compound of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The compound of the present invention may be administered either simultaneously with, or before or after, one or more therapeutic co-agent(s) (co-therapeutic agents). Suitable co-therapeutic agents for use in the invention include, for example, cancer chemotherapeutics including but not limited to inhibitors of PI3K, other inhibitors of the Raf pathway, paclitaxel, docetaxel, temozolomide, platins, doxorubicins, vinblastins, cyclophosphamide, topotecan, gemcitabine, ifosfamide, etoposide, irinotecan, and the like. The compound of the present invention may be administered separately, by the same or different route of administration, or together in the same pharmaceutical composition as the co-agent(s).

In one embodiment, the invention provides a product comprising a compound of formula I and at least one other therapeutic co-agent as a combined preparation for simultaneous, separate or sequential use in therapy. In one embodiment, the therapy is the treatment of a disease or condition mediated by B-Raf or C-Raf, such as cancer. Products provided as a combined preparation include a composition comprising the compound of formula I and the other therapeutic co-agent(s) together in the same pharmaceutical composition, or the compound of formula I and the other therapeutic co-agent(s) in separate form, e.g. in the form of a kit.

In one embodiment, the invention provides a pharmaceutical composition comprising a compound of formula I and another therapeutic co-agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of formula I. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic co-agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula I for treating a disease or condition mediated by B-Raf or C-Raf, wherein the medicament is prepared for administration with another therapeutic agent. The invention also provides the use of another therapeutic co-agent for treating a disease or condition, wherein the medicament is administered with a compound of formula I.

The invention also provides a compound of formula I for use in a method of treating a disease or condition mediated by B-Raf or C-Raf, wherein the compound of formula I is prepared for administration with another therapeutic agent. The invention also provides another therapeutic co-agent for use in a method of treating a disease or condition mediated by B-Raf or C-Raf, wherein the other therapeutic co-agent is prepared for administration with a compound of formula I. The invention also provides a compound of formula I for use in a method of treating a disease or condition mediated by B-Raf or C-Raf, wherein the compound of formula I is administered with another therapeutic co-agent. The invention also provides another therapeutic co-agent for use in a method of treating a disease or condition mediated by B-Raf or C-Raf, wherein the other therapeutic co-agent is administered with a compound of formula I.

The invention also provides the use of a compound of formula I for treating a disease or condition mediated by B-Raf or C-Raf, wherein the patient has previously (e.g. within 24 hours) been treated with another therapeutic agent. The invention also provides the use of another therapeutic agent for treating a disease or condition mediated by B-Raf or C-Raf, wherein the patient has previously (e.g. within 24 hours) been treated with a compound of formula I.

Processes for Making Compounds of the Invention

The present invention also includes a process for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Alternatively, the salt forms of the compounds of the invention can be prepared using salts of the starting materials or intermediates.

The free acid or free base forms of the compounds of the invention can be prepared from the corresponding base addition salt or acid addition salt form, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", $3^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

Insofar as the production of the starting materials is not particularly described, the compounds are known or can be prepared analogously to methods known in the art or as disclosed in the Example hereinafter.

One of skill in the art will appreciate that the above transformations are only representative of methods for preparation of the compounds of the present invention, and that other well known methods can similarly be used.

EXAMPLES

The present invention is further exemplified, but not limited, by the following intermediates and examples that illustrate the preparation of compounds of Formula I according to the invention.

The following abbreviations may be used herein:

| | |
|---|---|
| DAST | (diethylamino)sulfurtrifluoride |
| DCM | Dichloromethane |
| DIAD | diisopropylazodicarboxylate |
| DIEA | diisopropylethylamine |
| DMA | Dimethylacetamide |
| DMAP | 4-dimethylaminopyridine |
| DME | 1,2-dimethoxyethane |
| DMF | N,N-dimethylformamide |
| DPPF | 1,1'-bis(diphenylphosphino)ferrocene |
| EDC | 1-(3-Dimethylaminopropyl)-3-ethylcarbodiimide hydrochloride |
| EtOAc | ethyl acetate |
| EtOH | Ethanol |

| | |
|---|---|
| HOAT | Hydroxyazabenzotriazole |
| HOBt | Hydroxybenzotriazole |
| $K_2CO_3$ | Potassium carbonate |
| MeCN | Acetonitrile |
| $MgSO_4$ | Magnesium sulfate |
| MeOH | Methanol |
| $Na_2CO_3$ | sodium carbonate |
| NaCl | Sodium chloride |
| $NaHCO_3$ | sodium bicarbonate |
| NBS | N-bromosuccinimide |
| NMP | N-methyl-2-pyrrolidone |
| $Pd_2(dba)_3$ | Tris(dibenzylideneacetone)dipalladium(0) |
| $Pd(PPh_3)_4$ | Tetrakis(triphenylphospine)palladium(0) |
| $Pd(dppf)Cl_2$-DCM | Dichloro-(1,2-bis(diphenylphosphino)ethan)-Palladium(II)-dichloromothethane adduct |
| RT or rt | room temperature |
| TBDMSCl | tert-butyldimethylsilylchloride |
| TEA | Triethylamine |
| THF | tetrahydrofuran |
| THP | tetrahydropyran |

Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

Mass spectrometric analysis was performed on LCMS instruments: Waters System (Acuity UPLC and a Micromass ZQ mass spectrometer; Column: Acuity HSS C18 1.8-micron, 2.1×50 mm; gradient: 5-95% acetonitrile in water with 0.05% TFA over a 1.8 min period; flow rate 1.2 mL/min; molecular weight range 200-1500; cone Voltage 20 V; column temperature 50° C.). All masses were reported as those of the protonated parent ions.

Nuclear magnetic resonance (NMR) analysis was performed on some of the compounds with a Varian 400 MHz NMR (Palo Alto, Calif.). The spectral reference was either TMS or the known chemical shift of the solvent.

All starting materials, building blocks, reagents, acids, bases, dehydrating agents, solvents, and catalysts utilized to synthesize the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art in view of the following examples.

Method 1

Synthesis of 4-Pyridinyl-Phenyl/3-Pyridinyl Amides as Intermediates

Scheme I

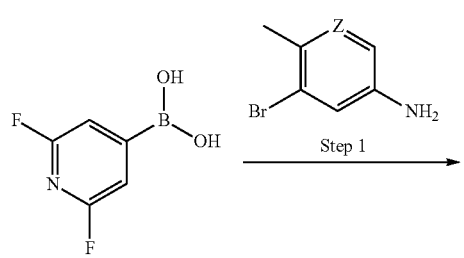

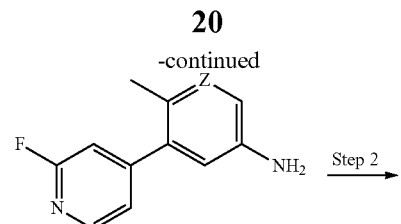

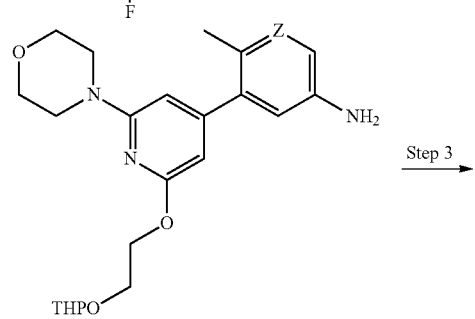

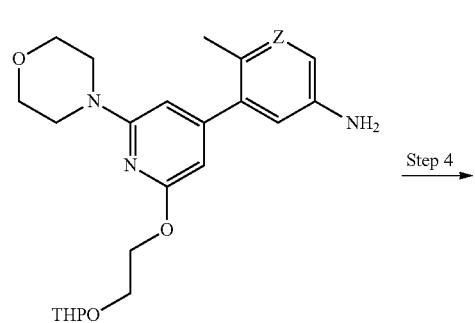

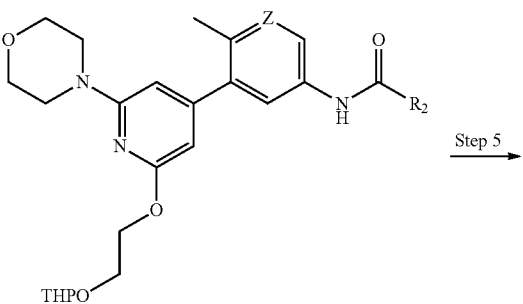

wherein Z is selected from CH and N; and $R_2$ is selected from pyridinyl and phenyl; wherein phenyl and pyridinyl can be substituted with a group selected from trifluoromethyl, 1,1-difluoroethyl and 2-fluoropropan-2-yl.

Intermediate 1

Synthesis of N-(3-(6-(2-hydroxyethoxy)-5-morpholinopyridin-3-yl)-4-methylphenyl)-3-(trifluoromethyl)benzamide

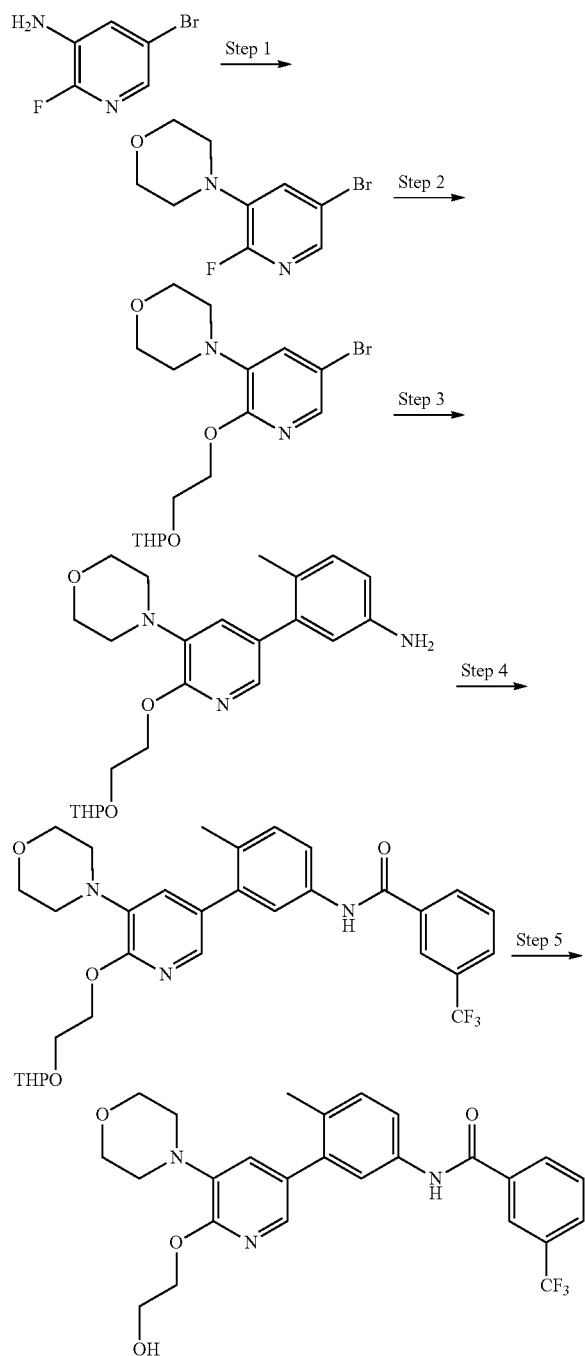

Step 1:

To an ice-bath cooled solution of NaH (60% in mineral oil, 3.0 equiv.) in DMF (1.4 M) was added 3-amino-5-bromo-2-fluoropyridine (1.0 equiv.). The mixture was allowed to warm to room temperature over 15 min and then treated with bis(2-bromoethyl) ether (1.5 equiv.). The mixture was heated to 80° C. and stirred for 35 min. The cooled reaction mixture was poured into four volumes of water. The resulting precipitate was collected by vacuum filtration. The filter cake was rinsed twice with water and twice with heptanes. The tan solid was dried under high vacuum to give 4-(5-bromo-2-fluoropyridin-3-yl)morpholine (83% yield). LCMS (m/z) (M+H)=260.9/262.9, Rt=0.74 min.

Step 2:

2-((Tetrahydro-2H-pyran-2-yl)oxy)ethanol (5.0 equiv.) was added dropwise to a stirred suspension of 60% NaH (5.0 equiv.) in dioxane (0.5 M). The mixture was stirred for 20 min followed by the addition of (4-(5-bromo-2-fluoropyridin-3-yl)morpholine (1.00 equiv.) and the reaction mixture was heated at 105° C. for 2.75 hrs. The cooled reaction mixture quenched with water and extracted twice with EtOAc. The combined organics were dried over $MgSO_4$, filtered and concentrated. The crude was purified by flash chromatography over silica gel (EtOAc in heptane 0-17% gradient) to 4-(5-bromo-2-(2-((tetrahydro-2H-pyran-2-yl)oxy)ethoxy)pyridin-3-yl)morpholine (86% yield). 1H NMR (400 MHz, Methylene Chloride-d2) δ 7.82 (d, J=2.2 Hz, 1H), 7.21 (d, J=2.2 Hz, 1H), 4.71-4.66 (m, 1H), 4.57-4.45 (m, 2H), 4.07 (ddd, J=11.3, 5.9, 3.4 Hz, 1H), 3.94-3.82 (m, 5H), 3.82-3.74 (m, 1H), 3.52 (tddd, J=9.5, 7.9, 3.6, 2.4 Hz, 1H), 3.18-3.10 (m, 4H), 1.89-1.66 (m, 2H), 1.66-1.48 (m, 4H). LCMS (m/z) (M+H)=389.2, Rt=1.42 min.

Step 3:

To a 0.5 M solution of 4-(5-bromo-2-(2-((tetrahydro-2H-pyran-2-yl)oxy)ethoxy)pyridin-3-yl)morpholine (1.0 equiv.) in dioxane was added 4-methyl-3-(4,4,5,5-tetramethyl-1,3,2-dioxaborolan-2-yl)aniline (1.4 equiv.), PdCl2(dppf).CH2Cl2 adduct (0.06 equiv.), and 2M aqueous sodium carbonate (3.00 equiv.). The reaction mixture was purged with nitrogen and then heated at 80° C. for 18 hrs. The cooled reaction mixture was poured onto water and extracted three time with EtOAc. The combined organics were washed with water and brine, dried over $MgSO_4$, filtered and concentrated. The crude was purified by flash chromatography over silica gel (EtOAc in heptane, 0-30% gradient) to give 4-methyl-3-(5-morpholino-6-(2-((tetrahydro-2H-pyran-2-yl)oxy)ethoxy)pyridin-3-yl)aniline (64.0% yield). 1H NMR (400 MHz, Methylene Chloride-d2) δ 7.72 (d, J=2.1 Hz, 1H), 7.14-6.99 (m, 2H), 6.63 (dd, J=8.0, 2.5 Hz, 1H), 6.58 (d, J=2.5 Hz, 1H), 4.74 (dd, J=4.1, 2.8 Hz, 1H), 4.65-4.48 (m, 2H), 4.13 (dd, J=6.5, 3.5 Hz, 1H), 3.97-3.78 (m, 6H), 3.78-3.63 (m, 2H), 3.63-3.47 (m, 1H), 3.27-3.06 (m, 4H), 2.18 (s, 3H), 1.92-1.70 (m, 2H), 1.69-1.47 (m, 4H). LCMS (m/z) (M+H)=414.4, Rt=1.30 min.

Step 4:

To a solution of 4-methyl-3-(5-morpholino-6-(2-((tetrahydro-2H-pyran-2-yl)oxy)ethoxy)pyridin-3-yl)aniline (1.0 equiv) and 3-(trifluoromethyl)benzoic acid (1.2 equiv.) in DMF (0.15 M) at 25° C. were added BOP (1.3 equiv.) and NMM (3 equiv) and the mixture was stirred for 18 h at 25° C. The mixture was poured onto brine and extracted four times with ethyl acetate. The combined organics were dried over $MgSO_4$, filtered and concentrated. The crude was purified by flash chromatography over silica gel (EtOAc in heptane 0-30% gradient) to N-(4-methyl-3-(5-morpholino-6-(2-((tetrahydro-2H-pyran-2-yl)oxy)ethoxy)pyridin-3-yl)phenyl)-3-(trifluoromethyl)benzamide (86% yield). 1H NMR (400 MHz, Methylene Chloride-d2) δ 8.65-8.51 (m, 1H), 8.19 (t, J=1.9 Hz, 1H), 8.10 (d, J=7.9 Hz, 1H), 7.82 (d, J=7.8 Hz, 1H), 7.73 (d, J=2.0 Hz, 1H), 7.66-7.58 (m, 2H), 7.52 (d, J=2.4 Hz, 1H), 7.28 (d, J=8.1 Hz, 1H), 7.08 (d, J=2.0 Hz, 1H), 4.73 (t, J=3.4 Hz, 1H), 4.66-4.50 (m, 2H), 4.11 (ddd, J=11.3, 5.9, 3.4 Hz, 1H), 3.97-3.76 (m, 6H), 3.60-3.48

(m, 1H), 3.21-3.08 (m, 4H), 2.29 (s, 3H), 1.92-1.68 (m, 2H), 1.68-1.48 (m, 4H). LCMS (m/z) (M+H)=586.3, Rt=1.63 min.

Step 5:

To a solution of the N-(4-methyl-3-(5-morpholino-6-(2-((tetrahydro-2H-pyran-2-yl)oxy)ethoxy)pyridin-3-yl)phenyl)-3-(trifluoromethyl)benzamide (1.0 equiv) in MeOH (0.15 M) at 25° C. was HCl (4 M in dioxane, 12 equiv) and the mixture was stirred for 30 min at 25° C. The mixture was concentrated and then partitioned between saturated aqueous NaHCO$_3$ and ethyl acetate. The combined organics were washed with saturated aqueous NaHCO$_3$ and brine, dried over MgSO$_4$, filtered and concentrated. The crude was purified by preparative HPLC (X-Bridge 30×50 mm 5 um column, 35-60% ACN/H$_2$O gradient w/ 5 mM NH$_4$OH) to N-(3-(6-(2-hydroxyethoxy)-5-morpholinopyridin-3-yl)-4-methylphenyl)-3-(trifluoromethyl)benzamide (66% yield). 1H NMR (400 MHz, Methylene Chloride-d2) δ 8.06 (s, 1H), 7.98 (d, J=7.8 Hz, 1H), 7.88 (s, 1H), 7.77-7.71 (m, 1H), 7.63 (d, J=2.1 Hz, 1H), 7.57 (t, J=7.8 Hz, 1H), 7.50 (dd, J=8.2, 2.3 Hz, 1H), 7.39 (d, J=2.3 Hz, 1H), 7.21 (d, J=8.3 Hz, 1H), 7.04 (d, J=2.0 Hz, 1H), 4.50-4.44 (m, 2H), 3.87-3.82 (m, 2H), 3.79-3.72 (m, 4H), 3.08-2.99 (m, 4H), 2.18 (s, 3H). LCMS (m/z) (M+H)=502.3, Rt=1.40 min.

Intermediate 2

Synthesis of (R)—N-(3-(2-(2-hydroxyethoxy)-6-(3-methylmorpholino)pyridin-4-yl)-4-methylphenyl)-3-(trifluoromethyl)benzamide

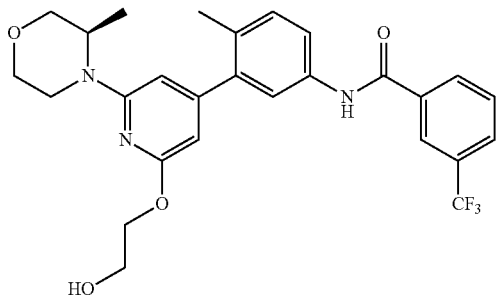 [SMILES: Cc1ccc(NC(=O)c2cccc(C(F)(F)F)c2)cc1-c1cc(OCCO)nc(N2CCOC[C@H]2C)c1]

Step 1:

To a 0.3M solution of 3-bromo-4-methylaniline (1.1 equiv.) in DME was added (2,6-difluoropyridin-4-yl)boronic acid (1.0 equiv.), PdCl2(dppf).CH2Cl2 adduct (0.05 equiv.), and 2M aqueous sodium carbonate (3.00 equiv.). The reaction mixture was heated at 80° C. for 2 hrs. The cooled reaction mixture was partitioned between water and EtOAc. The combined organics were washed with brine, dried over MgSO$_4$, filtered and concentrated. The crude was purified by flash chromatography over silica gel (EtOAc in heptane, 0-60% gradient) to give 3-(2,6-difluoropyridin-4-yl)-4-methylaniline (95.0% yield). LCMS (m/z) (M+H)=221.2, Rt=0.95 min.

Step 2:

To a 0.5 M solution of 3-(2,6-difluoropyridin-4-yl)-4-methylaniline (1.00 eq) and Huenig's base (2.0 eq) in DMSO was added (R)-4-methylmorpholine (1.6 eq). The reaction was mixture was heated to 100° C. for 18 hrs. The reaction was partition between water and EtOAc. The aqueous was further washed with EtOAc. The combined organics were washed with brine, dried over MgSO$_4$, filtered, and concentrated. The crude was purified by flash chromatography over silica gel (EtOAc in heptane, 0-40% gradient) to give (R)-3-(2-fluoro-6-(3-methylmorpholino)pyridin-4-yl)-4-methylaniline (90%). LCMS (m/z) (M+H)=302.0, Rt=1.01 min.

Step 3:

2-((Tetrahydro-2H-pyran-2-yl)oxy)ethanol (4.0 equiv.) was added dropwise to a stirred suspension of 60% NaH (4.0 equiv.) in dioxane (1.0 M). The mixture was stirred for 20 min followed by the addition of (R)-3-(2-fluoro-6-(3-methylmorpholino)pyridin-4-yl)-4-methylaniline (1.00 equiv.) and the reaction mixture was heated at 100° C. for 4 hrs. The cooled reaction mixture quenched with water and extracted three times with EtOAc. The combined organics were washed with brine, dried over MgSO$_4$, filtered and concentrated. The crude was purified by flash chromatography over silica gel (EtOAc in heptane 0-60% gradient) to 4-methyl-3-(2-((R)-3-methylmorpholino)-6-(2-((tetrahydro-2H-pyran-2-yl)oxy)ethoxy)pyridin-4-yl)aniline (95% yield). LCMS (m/z) (M+H)=482.2, Rt=1.14 min.

Step 4:

To a solution of 4-methyl-3-(2-((R)-3-methylmorpholino)-6-(2-((tetrahydro-2H-pyran-2-yl)oxy)ethoxy)pyridin-4-yl)aniline (1.0 equiv) and 3-(trifluoromethyl)benzoic acid (1.1 equiv.) in DMA (0.3 M) at 25° C. were added HOAT (1.3 equiv.), i-Pr$_2$NEt (3 equiv.), and EDC (1.3 equiv) and the mixture was stirred for 3 h at 25° C. The mixture was poured onto water and extracted three times with ethyl acetate. The combined organics were washed with water, brine, dried over MgSO$_4$, filtered and concentrated. The crude was purified by flash chromatography over silica gel (MeOH in DCM 0-10% gradient) to N-(4-methyl-3-(2-((R)-3-methylmorpholino)-6-(2-((tetrahydro-2H-pyran-2-yl)oxy)ethoxy)pyridin-4-yl)phenyl)-3-(trifluoromethyl)benzamide (71% yield). LCMS (m/z) (M+H)=600.3, Rt=1.67 min.

Step 5:

To a solution of the N-(4-methyl-3-(2-((R)-3-methylmorpholino)-6-(2-((tetrahydro-2H-pyran-2-yl)oxy)ethoxy)pyridin-4-yl)phenyl)-3-(trifluoromethyl)benzamide (1.0 equiv) in MeOH (0.3 M) at 25° C. was 4 M aq HCl (100 equiv) and the mixture was stirred for 3 h at 25° C. The mixture was poured onto saturated aqueous NaHCO$_3$ and extracted three times with ethyl acetate. The combined organics were washed with brine, dried over MgSO$_4$, filtered and concentrated. The crude was purified by flash chromatography over silica gel (EtOAc in heptane 0-10% gradient) to N-(4-methyl-3-(2-((R)-3-methylmorpholino)-6-(2-((tetrahydro-2H-pyran-2-yl)oxy)ethoxy)pyridin-4-yl)phenyl)-3-(trifluoromethyl)benzamide (71% yield). 1H NMR (400 MHz, Methanol-d4) δ ppm 8.28-8.16 (m, 1H), 7.88 (d, J=7.8 Hz, 1H), 7.72 (t, J=7.8 Hz, 1H), 7.65-7.54 (m, 1H), 7.27 (d, J=8.3 Hz, 1H), 6.16 (s, 1H), 6.07 (s, 1H), 4.39-4.32 (m, 2H), 3.98 (dd, J=11.3, 3.5 Hz, 1H), 3.91-3.70 (m, 3H), 3.60 (td, J=11.8, 3.1 Hz, 1H), 3.18 (td, J=12.6, 3.8 Hz, 1H), 2.26 (s, 2H), 1.23 (d, J=6.7 Hz, 2H). LCMS (m/z) (M+H)=516.2, Rt=1.42 min.

The following intermediates of Table 1 were prepared via Method 1 using the appropriate starting materials:

TABLE 1

| Intermediate | Structure | Name | Physical Data |
|---|---|---|---|
| 3 | 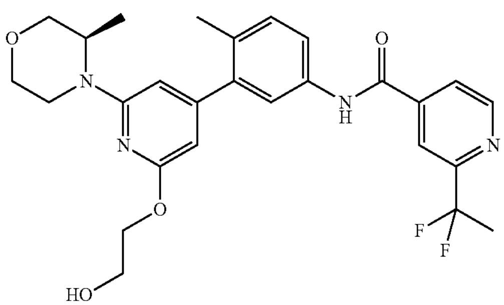 [SMILES: Cc1ccc(NC(=O)c2ccnc(C(C)(F)F)c2)cc1-c1cc(OCCO)nc(N2CCOC[C@H]2C)c1] | (R)-2-(1,1-difluoroethyl)-N-(3-(2-(2-hydroxyethoxy)-6-(3-methylmorpholino)pyridin-4-yl)-4-methylphenyl)isonicotinamide | 1H NMR (400 MHz, Methanol-d4) δ ppm 8.79 (dd, J = 4.8, 2.2 Hz, 0H), 8.17 (s, 0H), 7.98-7.91 (m, 0H), 7.66-7.55 (m, 1H), 7.27 (dd, J = 8.3, 3.7 Hz, 0H), 6.15 (d, J = 1.7 Hz, 0H), 6.06 (d, J = 1.4 Hz, 0H), 4.39-4.32 (m, 1H), 3.97 (d, J = 11.2 Hz, 0H), 3.90-3.83 (m, 1H), 3.78 (dd, J = 18.6, 7.0 Hz, 1H), 3.65-3.54 (m, 0H), 3.23-3.12 (m, 0H), 2.25 (d, J = 2.2 Hz, 1H), 2.03 (t, J = 18.7 Hz, 1H), 1.23 (dd, J = 6.7, 1.5 Hz, 1H). LCMS (m/z) (M + H) = 513.2, Rt = 1.29 min. |
| 4 | 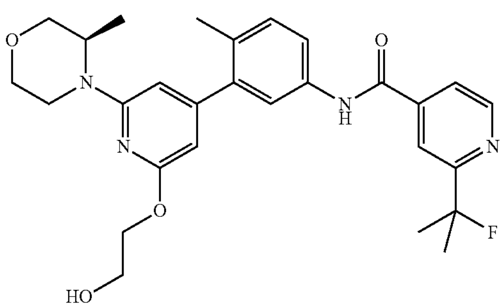 [SMILES: Cc1ccc(NC(=O)c2ccnc(C(C)(C)F)c2)cc1-c1cc(OCCO)nc(N2CCOC[C@H]2C)c1] | (R)-2-(2-fluoropropan-2-yl)-N-(3-(2-(2-hydroxyethoxy)-6-(3-methylmorpholino)pyridin-4-yl)-4-methylphenyl)isonicotinamide | 1H NMR (400 MHz, Methanol-d4) δ ppm 8.69 (d, J = 5.1 Hz, 1H), 8.05 (s, 0H), 7.76 (d, J = 5.1 Hz, 1H), 7.67-7.55 (m, 1H), 7.28 (d, J = 8.3 Hz, 1H), 6.16 (s, 1H), 6.06 (s, 1H), 4.39-4.32 (m, 2H), 3.98 (dd, J = 11.3, 3.3 Hz, 1H), 3.90-3.83 (m, 1H), 3.85-3.70 (m, 2H), 3.60 (td, J = 11.8, 2.9 Hz, 1H), 3.18 (td, J = 12.6, 3.7 Hz, 1H), 2.26 (s, 2H), 1.75 (s, 2H), 1.70 (s, 2H), 1.23 (d, J = 6.7 Hz, 2H). LCMS (m/z) (M + H) = 509.2, Rt = 1.29 min. |
| 5 | 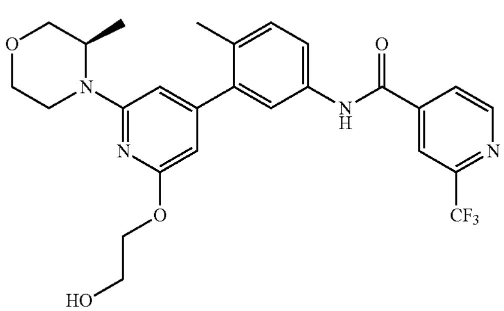 [SMILES: Cc1ccc(NC(=O)c2ccnc(C(F)(F)F)c2)cc1-c1cc(OCCO)nc(N2CCOC[C@H]2C)c1] | (R)-N-(3-(2-(2-hydroxyethoxy)-6-(3-methylmorpholino)pyridin-4-yl)-4-methylphenyl)-2-(trifluoromethyl)isonicotinamide | 1H NMR (400 MHz, Methanol-d4) δ ppm 8.89 (d, J = 5.0 Hz, 1H), 8.29 (s, 1H), 8.11 (dd, J = 5.0, 1.2 Hz, 1H), 7.67-7.56 (m, 1H), 7.27 (d, J = 8.3 Hz, 1H), 6.15 (s, 1H), 6.08-6.03 (m, 1H), 4.39-4.31 (m, 2H), 3.97 (dd, J = 11.3, 3.5 Hz, 1H), 3.90-3.70 (m, 3H), 3.60 (td, J = 11.9, 3.1 Hz, 1H), 3.17 (td, J = 12.6, 3.8 Hz, 1H), 2.25 (s, 2H), 1.23 (d, J = 6.7 Hz, 2H). LCMS (m/z) (M + H) = 517.1, Rt = 1.32 min. |
| 6 | 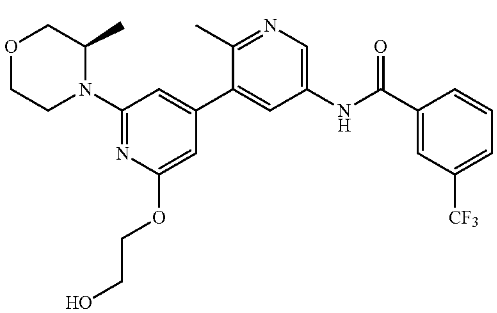 [SMILES: Cc1ncc(NC(=O)c2cccc(C(F)(F)F)c2)cc1-c1cc(OCCO)nc(N2CCOC[C@H]2C)c1] | (R)-N-(2'-(2-hydroxyethoxy)-2-methyl-6'-(3-methylmorpholino)-[3,4'-bipyridin]-5-yl)-3-(trifluoromethyl)benzamide | 1H NMR (400 MHz, Methanol-d4) δ ppm 8.83 (d, J = 2.5 Hz, 1H), 8.29 (d, J = 2.0 Hz, 1H), 8.23 (d, J = 7.9 Hz, 1H), 8.09 (d, J = 2.5 Hz, 1H), 7.95-7.88 (m, 1H), 7.74 (t, J = 7.8 Hz, 1H), 6.21 (d, J = 1.0 Hz, 1H), 6.10 (d, J = 1.0 Hz, 1H), 4.37 (dd, J = 5.8, 4.2 Hz, 3H), 3.98 (dd, J = 11.4, 3.6 Hz, 1H), 3.94-3.83 (m, 3H), 3.83-3.71 (m, 2H), 3.61 (td, J = 11.8, 3.1 Hz, 1H), 3.20 (td, J = 12.6, 3.8 Hz, 1H), 2.48 (s, 3H), 1.24 (d, J = 6.6 Hz, 3H). LCMS (m/z) (M + H) = 517.0, Rt = 1.14 min. |

TABLE 1-continued

| Intermediate | Structure | Name | Physical Data |
|---|---|---|---|
| 7 | 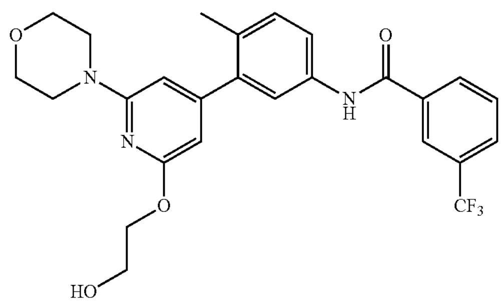 [SMILES: Cc1ccc(NC(=O)c2cccc(C(F)(F)F)c2)cc1-c1cc(OCCO)nc(N2CCOCC2)c1] | N-(3-(2-(2-hydroxyethoxy)-6-morpholinopyridin-4-yl)-4-methylphenyl)-3-(trifluoromethyl)benzamide | 1H NMR (400 MHz, Methanol-d4) δ ppm 8.26 (t, J = 1.8 Hz, 1H), 8.20 (dd, J = 7.7, 1.6 Hz, 1H), 7.89 (dt, J = 7.8, 1.2 Hz, 1H), 7.72 (t, J = 7.8 Hz, 1H), 7.66-7.52 (m, 2H), 7.27 (d, J = 8.3 Hz, 1H), 6.23 (d, J = 1.0 Hz, 1H), 6.12 (d, J = 0.9 Hz, 1H), 4.43-4.30 (m, 2H), 3.93-3.83 (m, 2H), 3.79 (dd, J = 5.7, 4.0 Hz, 4H), 3.55-3.44 (m, 4H), 2.26 (s, 3H). LCMS (m/z) (M + H) = 502.1, Rt = 1.52 min. |
| 8 | 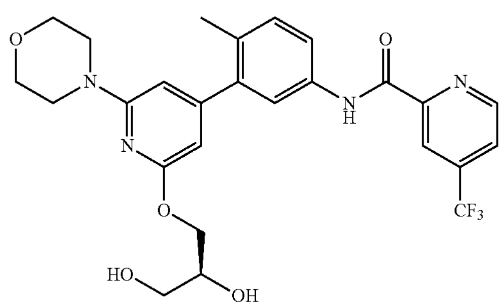 [SMILES: Cc1ccc(NC(=O)c2cc(C(F)(F)F)ccn2)cc1-c1cc(OC[C@@H](O)CO)nc(N2CCOCC2)c1] | (S)-N-(3-(2-(2,3-dihydroxypropoxy)-6-morpholinopyridin-4-yl)-4-methylphenyl)-4-(trifluoromethyl)picolinamide | $^1$H NMR (400 MHz, Methylene Chloride-d$_2$) δ 9.96 (s, 1H), 8.86 (d, J = 5.0 Hz, 1H), 8.54 (dt, J = 1.7, 0.8 Hz, 1H), 7.80-7.73 (m, 2H), 7.65 (d, J = 2.3 Hz, 1H), 7.34 (d, J = 8.3 Hz, 1H), 6.23 (d, J = 1.0 Hz, 1H), 6.18 (d, J = 0.9 Hz, 1H), 4.50-4.40 (m, 2H), 4.08 (tt, J = 5.8, 4.3 Hz, 1H), 3.87-3.81 (m, 4H), 3.81-3.67 (m, 2H), 3.54 (dd, J = 5.9, 4.0 Hz, 4H), 2.31 (s, 3H). LCMS (m/z) (M + H) = 533.0, Rt = 1.41 min. |

Example 1

2-((4-(2-methyl-5-(2-(trifluoromethyl)isonicotinamido)phenyl)-6-morpholinopyridin-2-yl)oxy)ethyl dihydrogen phosphate

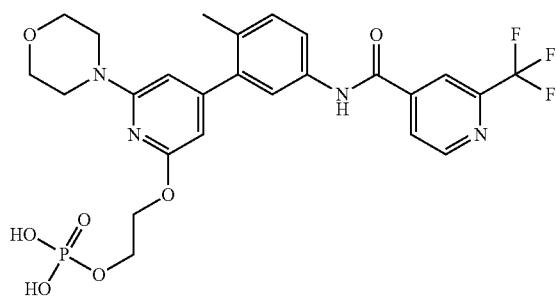 [SMILES: Cc1ccc(NC(=O)c2ccnc(C(F)(F)F)c2)cc1-c1cc(OCCOP(=O)(O)O)nc(N2CCOCC2)c1]

To a stirred solution of N-(3-(2-(2-hydroxyethoxy)-6-morpholinopyridin-4-yl)-4-methylphenyl)-2-(trifluoromethyl)isonicotinamide (1.0 equiv.) in THF (0.2 M) at −78° C. was added 2,6-lutidine (2.5 equiv.), and then POCl$_3$ (2.0 equiv.) was added dropwise. The mixture was stirred at −78° C. for 1.5 h and then quenched slowly with saturated aqueous NaHCO$_3$ and allowed to warm to RT. The mixture was poured into a separatory funnel and washed twice with DCM. The obtained aqueous layer was acidified to pH 3 with 6 M HCl and extracted twice with EtOAc. The combined organics were washed with brine, dried over MgSO$_4$, filtered, and concentrated. The residue was taken up in minimal H$_2$O, and then saturated aqueous Na$_2$CO$_3$ was titrated in until the mixture had a pH of 10. The mixture was stirred for 30 minutes, diluted with MeOH, adsorbed onto Celite and dry-loaded onto a C18 column pre-equilibrated with water. Alternatively, the reaction mixture was quenched slowly with a small amount of water and allowed to warm to RT. Saturated aqueous Na$_2$CO$_3$ was then titrated into the mixture until the it had a pH of 10. The mixture was stirred for 15 min, and then diluted with MeOH, adsorbed onto Celite, and dry-loaded onto a C18 column pre-equilibrated with water. Purification was carried out via flash chromatography eluting with water and 0-40% acetonitrile gradient. Pure product fractions were combined and lyophilized. Isolated 2-((4-(2-methyl-5-(2-(trifluoromethyl)isonicotinamido)phenyl)-6-morpholinopyridin-2-yl)oxy)ethyl dihydrogen phosphate was as the corresponding sodium salt in 40% yield. Optionally and additionally, this material could be recrystallized from 95% EtOH/water to provide pure, crystalline material after drying for 72 h in a 40° C. vacuum oven. $^1$H NMR (400 MHz, <cd3od>) δ ppm 2.26 (s, 3H) 3.45-3.54 (m, 4H) 3.74-3.83 (m, 4H) 4.16 (q, J=5.60 Hz, 2H) 4.47 (t, J=5.40 Hz, 2H) 6.06 (s, 1H) 6.19 (s, 1H) 7.29 (d, J=8.53 Hz, 1H) 7.54 (d, J=2.26 Hz, 1H) 7.70 (dd, J=8.28, 2.26 Hz, 1H) 8.13 (dd, J=5.02, 1.00 Hz, 1H) 8.30 (s, 1H) 8.90 (d, J=5.02 Hz, 1H) LCMS (m/z) (M+H)=583.3, Rt=1.33 min.

Example 2

(R)-2-((4-(2-methyl-5-(3-(trifluoromethyl)benzamido)phenyl)-6-(3-methylmorpholino)pyridin-2-yl)oxy)ethyl dihydrogen phosphate

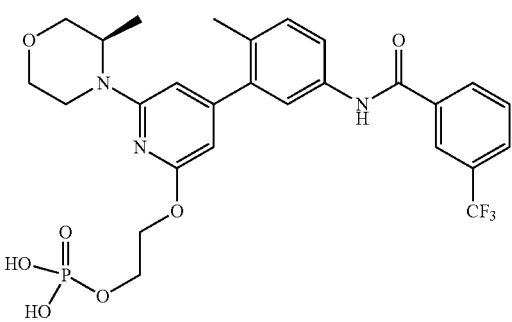 [SMILES: Cc1ccc(NC(=O)c2cccc(C(F)(F)F)c2)cc1-c1cc(OCCOP(=O)(O)O)nc(N2CCOC[C@H]2C)c1]

To a stirred solution of N-(4-methyl-3-(2-((R)-3-methylmorpholino)-6-(2-((tetrahydro-2H-pyran-2-yl)oxy)ethoxy)pyridin-4-yl)phenyl)-3-(trifluoromethyl)benzamide (1.0 equiv.) in THF (0.2 M) at −78° C. was added 2,6-lutidine (2.5 equiv.), and then POCl$_3$ (2.0 equiv.) was added dropwise. The mixture was stirred at −78° C. for 1.5 h and then quenched slowly with a small amount of water and allowed to warm to RT. Saturated aqueous Na$_2$CO$_3$ was then titrated into the mixture until the it had a pH of 10. The mixture was stirred for 15 min, and then diluted with MeOH, adsorbed onto Celite, and dry-loaded onto a C18 column pre-equilibrated with water. Purification was carried out via flash chromatography eluting with water and 0-40% acetonitrile gradient. Pure product fractions were combined and lyophilized. Isolated (R)-2-((4-(2-methyl-5-(3-(trifluoromethyl)benzamido)phenyl)-6-(3-methylmorpholino)pyridin-2-yl)oxy)ethyl dihydrogen phosphate as the corresponding sodium salt in 54% yield. $^1$H NMR (400 MHz, METHANOL-d$_4$) δ ppm 1.22 (d, J=6.53 Hz, 3H) 2.25 (s, 3H) 3.17 (td, J=12.67, 3.76 Hz, 1H) 3.60 (td, J=11.80, 3.01 Hz, 1H) 3.70-3.81 (m, 2H) 3.86 (d, J=13.05 Hz, 1H) 3.97 (dd, J=11.04, 3.01 Hz, 1H) 4.16 (q, J=5.52 Hz, 2H) 4.36 (d, J=6.53 Hz, 1H) 4.40-4.55 (m, 2H) 6.02 (s, 1H) 6.13 (s, 1H) 7.27 (d, J=8.53 Hz, 1H) 7.51 (d, J=2.01 Hz, 1H) 7.67 (dd, J=8.03, 2.01 Hz, 1H) 7.69-7.76 (m, 1H) 7.88 (d, J=7.53 Hz, 1H) 8.20 (d, J=7.53 Hz, 1H) 8.26 (s, 1H). LCMS (m/z) (M+H)=595.9, Rt=0.86 min.

Example 3

(R)-2-hydroxy-3-((4-(2-methyl-5-(4-(trifluoromethyl)picolinamido)phenyl)-6-morpholinopyridin-2-yl)oxy)propyl dihydrogen phosphate

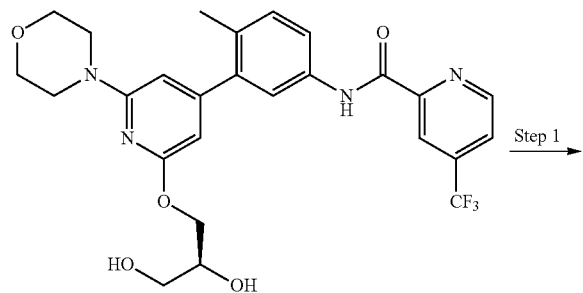

Step 1:

To a stirred solution of (S)—N-(3-(2-(2,3-dihydroxypropoxy)-6-morpholinopyridin-4-yl)-4-methylphenyl)-4-(trifluoromethyl)picolinamide (1.0 equiv.) in pyridine (0.2 M) at −20° C. was added di-tert-butyl phosphorobromidate (6 equiv.). The mixture was stirred at −20° C. for 10 min and then quenched with MeOH and allowed to warm to RT. The mixture was concentrated and then partitioned between water and ethyl acetate. The combined organics were washed with saturated aqueous NaHCO$_3$ and brine, dried over MgSO$_4$, filtered and concentrated. The crude was purified by preparative HPLC (X-Bridge 30×50 mm 5 um column, 55-80% ACN/H$_2$O gradient w/ 5 mM NH$_4$OH) to (R)-di-tert-butyl-(2-hydroxy-3-((4-(2-methyl-5-(4-(trifluoromethyl)picolinamido)phenyl)-6-morpholinopyridin-2-yl)oxy)propyl)phosphate (73% yield). (M+H)=725.3, Rt=1.65 min.

Step 2:

To a stirred solution of (R)-di-tert-butyl-(2-hydroxy-3-((4-(2-methyl-5-(4-(trifluoromethyl)picolinamido)phenyl)-6-morpholinopyridin-2-yl)oxy)propyl)phosphate (1.0 equiv.) in MeOH (0.5 M) at 0° C. was added HCl (4 M in dioxane, 120 equiv.). The mixture was stirred at 0° C. for 1 h and then concentrated. The residue was taken up in MeCN/water, frozen, and lyophilized to (R)-2-hydroxy-3-((4-(2-methyl-5-(4-(trifluoromethyl)picolinamido)phenyl)-6-morpholinopyridin-2-yl)oxy)propyl dihydrogen phosphate (96% yield). $^1$H NMR (400 MHz, DMSO-d$_6$) δ 10.79 (s, 1H), 9.03 (d, J=5.0 Hz, 1H), 8.09 (dd, J=5.1, 1.1 Hz, 1H), 7.85 (dd, J=8.3, 2.3 Hz, 1H), 7.81 (d, J=2.2 Hz, 1H), 7.29 (d, J=8.4 Hz, 1H), 6.27 (s, 1H), 6.06 (d, J=0.7 Hz, 1H), 4.30 (dd, J=11.0, 4.8 Hz, 1H), 4.16 (dd, J=11.0, 6.0 Hz, 1H), 4.01 (p, J=5.5 Hz, 1H), 3.85 (tt, J=7.9, 3.8 Hz, 2H), 3.75-3.63 (m, 6H), 3.52-3.42 (m, 6H), 2.24 (s, 3H). (M+H)=613.1 Rt=1.36 min.

The following examples of Table 2 were prepared using methods similar to those described in the above examples using the appropriate starting materials.

TABLE 2

| Example | Structure | Name | Physical Data |
|---|---|---|---|
| 4 | 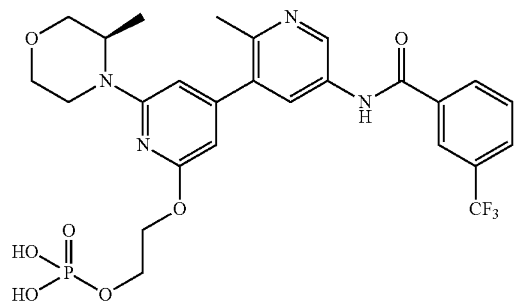 [SMILES: Cc1ncc(NC(=O)c2cccc(C(F)(F)F)c2)cc1-c1cc(OCCOP(=O)(O)O)nc(N2CCOC[C@H]2C)c1] | (R)-2-((2-methyl-6'-(3-methylmorpholino)-5-(3-(trifluoromethyl)-benzamido)-[3,4'-bipyridin]-2'-yl)oxy)-ethyl dihydrogen phosphate | $^1$H NMR (400 MHz, METHANOL-$d_4$) δ ppm 1.24 (d, J = 6.53 Hz,3 H) 2.47 (s,3 H) 3.14-3.26 (m, 1 H) 3.51-3.65 (m, 1 H) 3.70-3.82 (m, 2 H) 3.88 (d, J = 12.30 Hz, 1 H) 3.98 (dd, J = 11.04, 2.26 Hz, 1 H) 4.19 (d, J = 3.76 Hz, 2 H) 4.38 (d, J = 5.77 Hz, 1 H) 4.43-4.55 (m, 2 H) 6.06 (s, 1 H) 6.19 (s, 1 H) 7.75 (t, J = 7.78 Hz, 1 H) 7.91 (d, J = 7.78 Hz, 1 H) 8.05 (d, J = 2.01 Hz, 1 H) 8.25 (d, J = 7.78 Hz, 1 H) 8.29 (s, 1 H) 8.87 (d, J = 2.01 Hz, 1 H). LCMS (m/z) (M + H) = 597.0, Rt = 0.79 min. |
| 5 | 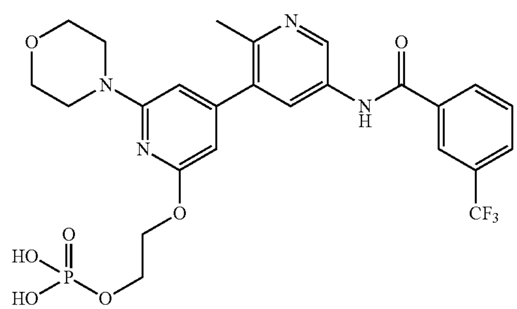 [SMILES: Cc1ncc(NC(=O)c2cccc(C(F)(F)F)c2)cc1-c1cc(OCCOP(=O)(O)O)nc(N2CCOCC2)c1] | 2-((2-methyl-6'-morpholino-5-(3-(trifluoromethyl)benzamido)-[3,4'-bipyridin]-2'-yl)oxy)ethyl dihydrogen phosphate | $^1$H NMR (400 MHz, METHANOL-$d_4$) δ ppm 2.47 (s, 3 H) 3.49-3.57 (m, 4 H) 3.73-3.85 (m, 4 H) 4.15 (q, J = 5.52 Hz, 2 H) 4.48 (t, J = 5.14 Hz, 2 H) 6.10 (s, 1 H) 6.25 (s, 1 H) 7.70-7.81 (m, 1 H) 7.91 (d, J = 7.78 Hz, 1 H) 8.04 (d, J = 2.51 Hz, 1 H) 8.24 (d, J = 7.78 Hz, 1 H) 8.29 (s, 1 H) 8.87 (d, J = 2.26 Hz, 1 H). LCMS (m/z) (M + H) = 583.1, Rt = 0.78 min. |
| 6 | 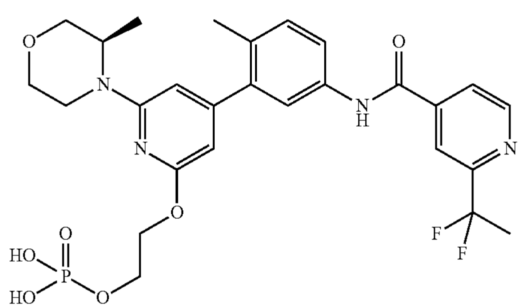 | (R)-2-((4-(5-(2-(1,1-difluoroethyl)isonicotinamido)-2-methylphenyl)-6-(3-methylmorpholino)pyridin-2-yl)oxy)ethyl dihydrogen phosphate | 1H NMR (400 MHz,METHANOL-$d_4$) δ ppm1.22 (d, J = 6.78 Hz, 3 H) 2.03 (t, J = 18.70 Hz, 3 H) 2.25 (s, 3 H) 3.17 (td, J = 12.67, 3.76 Hz, 1 H) 3.60 (td, J = 11.67, 3.01 Hz, 1 H) 3.69-3.79 (m, 2 H) 3.82-3.89 (m, 1 H) 3.97 (dd, J = 11.29, 3.26 Hz, 1 H) 4.15 (q, J = 5.35 Hz, 2 H) 4.35 (d, J = 6.53 Hz, 1 H) 4.41-4.54 (m, 2 H) 6.01 (s, 1 H) 6.13 (s, 1 H) 7.27 (d, J = 8.28 Hz, 1 H) 7.53 (d, J = 2.26 Hz, 1 H) 7.68 (dd, J = 8.28, 2.26 Hz, 1 H) 7.96 (dd, J = 5.02, 1.25 Hz, 1 H) 8.17 (s, 1 H) 8.79 (d, J = 5.02 Hz, 1 H). LCMS (m/z) (M + H) = 593.1, Rt = 0.84 min. |
| 7 | 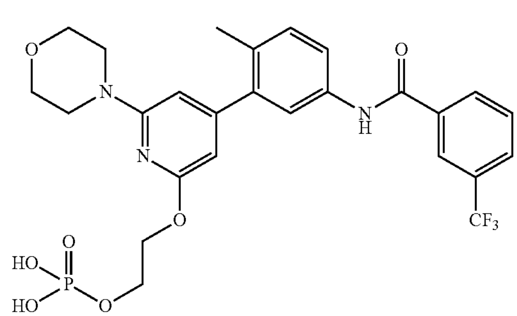 [SMILES: Cc1ccc(NC(=O)c2cccc(C(F)(F)F)c2)cc1-c1cc(OCCOP(=O)(O)O)nc(N2CCOCC2)c1] | 2-((4-(2-methyl-5-(3-(trifluoromethyl)benzamido)phenyl)-6-morpholinopyridin-2-yl)oxy)ethyl dihydrogen phosphate | $^1$H NMR (400 MHz, METHANOL-$d_4$) δ ppm 2.25 (s, 3 H) 3.46-3.54 (m, 4 H) 3.75-3.83 (m, 4 H) 4.17-4.28 (m, 2 H) 4.49 (t, J = 5.07 Hz, 2 H) 6.08 (d, J = 0.86 Hz, 1 H) 6.22 (d, J = 0.61 Hz, 1 H) 7.27 (d, J = 8.31 Hz, 1 H) 7.53 (d, J = 2.32 Hz, 1 H) 7.64 (dd, J = 8.25, 2.26 Hz, 1 H) 7.69-7.77 (m, 1 H) 7.88 (d, J = 7.82 Hz, 1 H) 8.20 (d, J = 7.95 Hz, 1 H) 8.25 (s, 1 H). LCMS (m/z) (M + H) = 582.0, Rt = 0.72 min. |

TABLE 2-continued

| Example | Structure | Name | Physical Data |
|---|---|---|---|
| 9 | 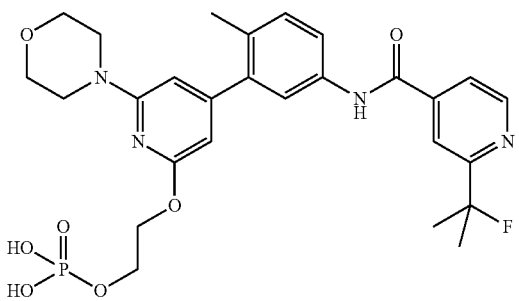 [SMILES: Cc1ccc(NC(=O)c2ccnc(C(C)(C)F)c2)cc1-c1cc(OCCOP(=O)(O)O)nc(N2CCOCC2)c1] | 2-((4-(5-(2-(2-fluoropropan-2-yl)isonicotinamido)-2-methylphenyl)-6-morpholinopyridin-2-yl)oxy)ethyl dihydrogen phosphate | $^1$H NMR (400 MHz, METHANOL-$d_4$) δ ppm 1.65-1.79 (m, 6 H) 2.25 (s, 3 H) 3.46-3.56 (m, 4 H) 3.73-3.83 (m, 4 H) 4.15 (q, J = 5.66 Hz, 2 H) 4.47 (t, J = 5.32 Hz, 2 H) 6.07 (s, 1 H) 6.19 (s, 1 H) 7.27 (d, J = 8.31 Hz, 1 H) 7.53 (d, J = 2.20 Hz, 1 H) 7.66 (dd, J = 8.25, 2.26 Hz, 1 H) 7.76 (dd, J = 5.07, 1.65 Hz, 1 H) 8.05 (s, 1 H) 8.68 (d, J = 5.14 Hz, 1 H). LCMS (m/z) (M + H) = 575.1, Rt = 0.74 min. |
| 10 | 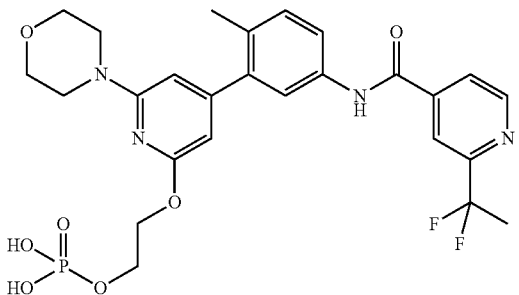 [SMILES: Cc1ccc(NC(=O)c2ccnc(C(C)(F)F)c2)cc1-c1cc(OCCOP(=O)(O)O)nc(N2CCOCC2)c1] | 2-((4-(5-(2-(1,1-difluoroethyl)isonicotinamido)-2-methylphenyl)-6-morpholinopyridin-2-yl)oxy)ethyl dihydrogen phosphate | $^1$H NMR (400 MHz, METHANOL-$d_4$) δ ppm 2.03 (t, J = 18.71 Hz, 3 H) 2.25 (s, 3 H) 3.44-3.57 (m, 4 H) 3.70-3.84 (m, 4 H) 4.11-4.21 (m, 2 H) 4.47 (t, J = 5.38 Hz, 2 H) 6.06 (d, J = 0.73 Hz, 1 H) 6.19 (s, 1 H) 7.28 (d, J = 8.44 Hz, 1 H) 7.52 (d, J = 2.32 Hz, 1 H) 7.68 (dd, J = 8.31, 2.32 Hz, 1 H) 7.96 (dd, J = 5.07, 1.53 Hz, 1 H) 8.17 (d, J = 0.73 Hz, 1 H) 8.79 (dd, J = 5.14, 0.61 Hz, 1 H). LCMS (m/z) (M + H) = 579.1, Rt = 0.72 min. |
| 11 | 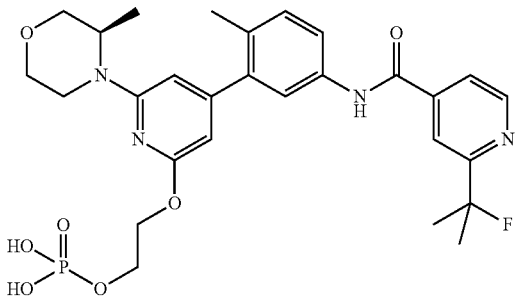 [SMILES: Cc1ccc(NC(=O)c2ccnc(C(C)(C)F)c2)cc1-c1cc(OCCOP(=O)(O)O)nc(N2CCOC[C@H]2C)c1] | (R)-2-((4-(5-(2-(2-fluoropropan-2-yl)isonicotinamido)-2-methylphenyl)-6-(3-methylmorpholino)pyridin-2-yl)oxy)ethyl dihydrogen phosphate | $^1$H NMR (400 MHz, METHANOL-$d_4$) δ ppm 1.23 (d, J = 6.60 Hz, 3 H) 1.66-1.79 (m, 6 H) 2.25 (s, 3 H) 3.18 (d, J = 3.42 Hz, 1 H) 3.60 (d, J = 2.69 Hz, 1 H) 3.71-3.80 (m, 2 H) 3.86 (d, J = 12.96 Hz, 1 H) 3.97 (dd, J = 11.25, 2.93 Hz, 1 H) 4.16 (q, J = 5.38 Hz, 2 H) 4.36 (d, J = 6.60 Hz, 1 H) 4.42-4.52 (m, 2 H) 6.02 (s, 1 H) 6.13 (s, 1 H) 7.27 (d, J = 8.31 Hz, 1 H) 7.52 (d, J = 1.96 Hz, 1 H) 7.67 (dd, J = 8.19, 2.08 Hz, 1 H) 7.76 (dd, J = 5.01, 1.34 Hz, 1 H) 8.05 (s, 1 H) 8.68 (d, J = 5.14 Hz, 1 H). LCMS (m/z) (M + H) = 589.3, Rt = 0.74 min. |
| 12 | 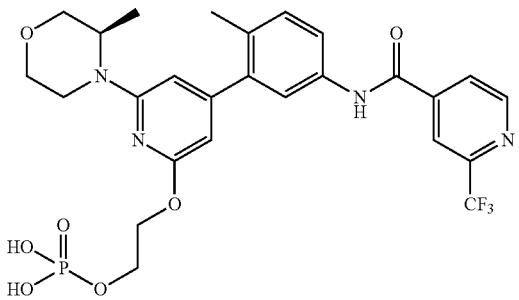 [SMILES: Cc1ccc(NC(=O)c2ccnc(C(F)(F)F)c2)cc1-c1cc(OCCOP(=O)(O)O)nc(N2CCOC[C@H]2C)c1] | (R)-2-((4-(2-methyl-5-(2-(trifluoromethyl)-isonicotinamido)phenyl)-6-(3-methylmorpholino)pyridin-2-yl)oxy)ethyl dihydrogen phosphate | $^1$H NMR (400 MHz, METHANOL-$d_4$) δ ppm 1.22 (d, J = 6.53 Hz, 3 H) 2.26 (s, 3 H) 3.08-3.22 (m, 1 H) 3.60 (td, J = 11.80, 3.01 Hz, 1 H) 3.69-3.80 (m, 2 H) 3.86 (d, J = 13.05 Hz, 1 H) 3.97 (dd, J = 11.29, 3.26 Hz, 1 H) 4.16 (q, J = 5.52 Hz, 2 H) 4.36 (d, J = 6.53 Hz, 1 H) 4.40-4.54 (m, 2 H) 6.01 (s, 1 H) 6.12 (s, 1 H) 7.28 (d, J = 8.53 Hz, 1 H) 7.53 (d, J = 2.01 Hz, 1 H) 7.70 (dd, J = 8.03, 2.01 Hz, 1 H) 8.13 (d, J = 4.52 Hz, 1 H) 8.30 (s, 1 H) 8.90 (d, J = 5.02 Hz, 1 H). LCMS (m/z) (M + H) = 597.0, Rt = 0.79 min. |

TABLE 2-continued

| Example | Structure | Name | Physical Data |
|---|---|---|---|
| 13 | 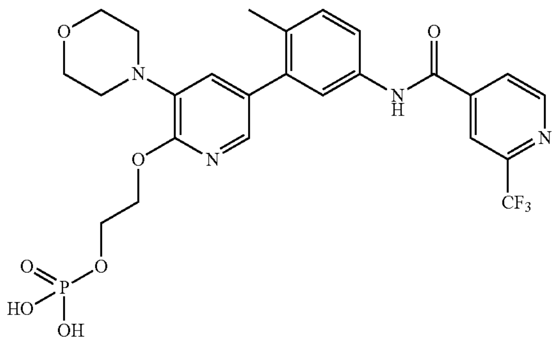 [SMILES: Cc1ccc(NC(=O)c2ccnc(C(F)(F)F)c2)cc1-c1cnc(OCCOP(=O)(O)O)c(N2CCOCC2)c1] | 2-((5-(2-methyl-5-(2-(trifluoromethyl)isonicotinamido)phenyl)-3-morpholinopyridin-2-yl)oxy)ethyl dihydrogen phosphate | $^1$H NMR (400 MHz, METHANOL-d$_4$) δ ppm 2.27 (s, 3 H) 3.10-3.18 (m, 4 H) 3.78-3.90 (m, 4 H) 4.22 (q, J = 5.61 Hz, 2 H) 4.59 (t, J = 5.40 Hz, 2 H) 7.15 (d, J = 2.26 Hz, 1 H) 7.31 (d, J = 8.28 Hz, 1 H) 7.54 (d, J = 2.26 Hz, 1 H) 7.69 (d, J = 2.01 Hz, 1 H) 7.71 (dd, J = 8.28, 2.26 Hz, 1 H) 8.13 (dd, J = 5.02, 1.00 Hz, 1 H) 8.30 (s, 1 H) 8.90 (d, J = 5.02 Hz, 1 H). LCMS (m/z) (M + H) = 583.0, Rt = 0.78 min. |
| 14 | 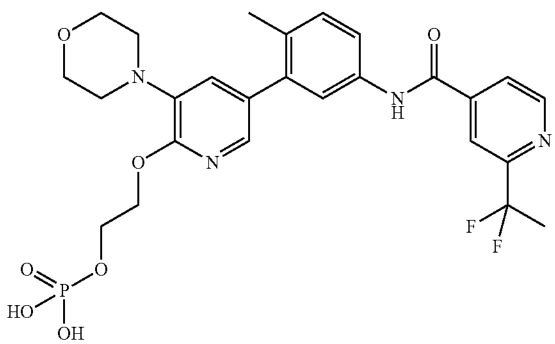 [SMILES: Cc1ccc(NC(=O)c2ccnc(C(C)(F)F)c2)cc1-c1cnc(OCCOP(=O)(O)O)c(N2CCOCC2)c1] | 2-((5-(5-(2-(1,1-difluoroethyl)isonicotinamido)-2-methylphenyl)-3-morpholinopyridin-2-yl)oxy)ethyl dihydrogen phosphate | $^1$H NMR (400 MHz, METHANOL-d$_4$) ppm 2.03 (t, J = 18.70 Hz, 3 H) 2.27 (s, 3 H) 3.08-3.19 (m, 4 H) 3.79-3.89 (m, 4 H) 4.22 (q, J = 5.77 Hz, 2 H) 4.59 (t, J = 5.40 Hz, 2 H) 7.16 (d, J = 2.01 Hz, 1 H) 7.30 (d, J = 8.53 Hz, 1 H) 7.53 (d, J = 2.26 Hz, 1 H) 7.66-7.73 (m, 2 H) 7.97 (dd, J = 5.02, 1.51 Hz, 1 H) 8.18 (s, 1 H) 8.80 (d, J = 5.02 Hz, 1 H). LCMS (m/z) (M + H) = 579.0, Rt = 0.76 min. |
| 15 | 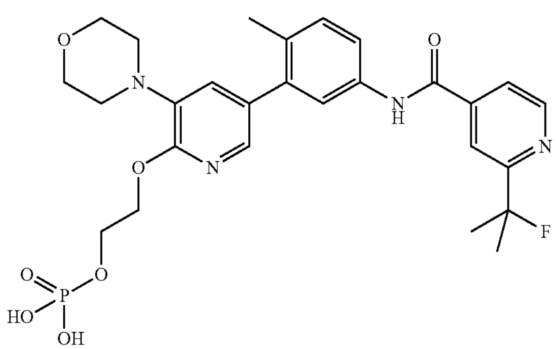 [SMILES: Cc1ccc(NC(=O)c2ccnc(C(C)(C)F)c2)cc1-c1cnc(OCCOP(=O)(O)O)c(N2CCOCC2)c1] | 2-((5-(5-(2-(2-fluoropropan-2-yl)isonicotinamido)-2-methylphenyl)-3-morpholinopyridin-2-yl)oxy)ethyl dihydrogen phosphate | $^1$H NMR (400 MHz, METHANOL-d$_4$) δ ppm 1.67-1.77 (m, 6 H) 2.27 (s, 3 H) 3.11-3.18 (m, 4 H) 3.81-3.89 (m, 4 H) 4.22 (q, J = 5.77 Hz, 2 H) 4.59 (t, J = 5.40 Hz, 2 H) 7.16 (d, J = 2.01 Hz, 1 H) 7.30 (d, J = 8.53 Hz, 1 H) 7.53 (d, J = 2.26 Hz, 1 H) 7.65-7.73 (m, 2 H) 7.77 (dd, J = 5.02, 1.51 Hz, 1 H) 8.06 (s, 1 H) 8.69 (d, J = 5.02 Hz, 1 H). LCMS (m/z) (M + H) = 575.0, Rt = 0.76 min. |
| 16 | 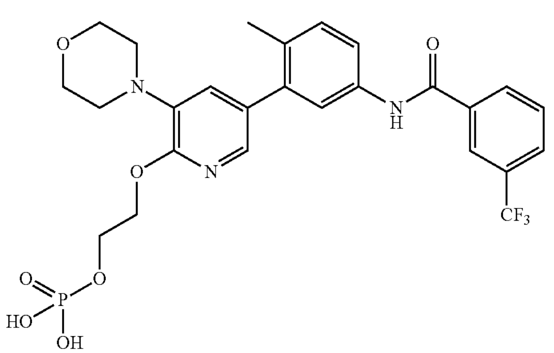 [SMILES: Cc1ccc(NC(=O)c2cccc(C(F)(F)F)c2)cc1-c1cnc(OCCOP(=O)(O)O)c(N2CCOCC2)c1] | 2-((5-(2-methyl-5-(3-(trifluoromethyl)benzamido)phenyl)-3-morpholinopyridin-2-yl)oxy)ethyl dihydrogen phosphate | $^1$H NMR (400 MHz, METHANOL-d$_4$) δ ppm 2.26 (s, 3 H) 3.11-3.17 (m, 4 H) 3.82-3.90 (m, 4 H) 4.22 (q, J = 5.77 Hz, 2 H) 4.59 (t, J = 5.40 Hz, 2 H) 7.16 (d, J = 2.01 Hz, 1 H) 7.29 (d, J = 8.28 Hz, 1 H) 7.53 (d, J = 2.26 Hz, 1 H) 7.65-7.76 (m, 3 H) 7.88 (d, J = 7.78 Hz, 1 H) 8.21 (d, J = 7.78 Hz, 1 H) 8.26 (s, 1 H). LCMS (m/z) (M + H) = 581.8, Rt = 0.71 min. |

TABLE 2-continued

| Example | Structure | Name | Physical Data |
|---|---|---|---|
| 17 | 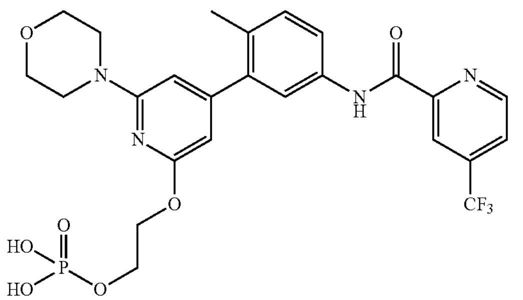 | 2-((4-(2-methyl-5-(4-(trifluoromethyl)picolinamido)phenyl)-6-morpholinopyridin-2-yl)oxy)ethyl dihydrogen phosphate | $^1$H NMR (400 MHz, METHANOL-d$_4$) δ ppm 2.25 (s, 3 H) 3.45-3.56 (m, 4 H) 3.75-3.84 (m, 4 H) 4.11-4.22 (m, 2 H) 4.48 (t, J = 5.26 Hz, 2 H) 6.08 (d, J = 0.86 Hz, 1 H) 6.21 (d, J = 0.86 Hz, 1 H) 7.29 (d, J = 8.31 Hz, 1 H) 7.65 (d, J = 2.32 Hz, 1 H) 7.72 (dd, J = 8.25, 2.38 Hz, 1 H) 7.90 (dt, J = 5.01, 0.86 Hz, 1 H) 8.37-8.46 (m, 1 H) 8.95 (d, J = 5.01 Hz, 1 H). LCMS (m/z) (M + H) = 583.0, Rt = 0.74 min. |
| 18 | 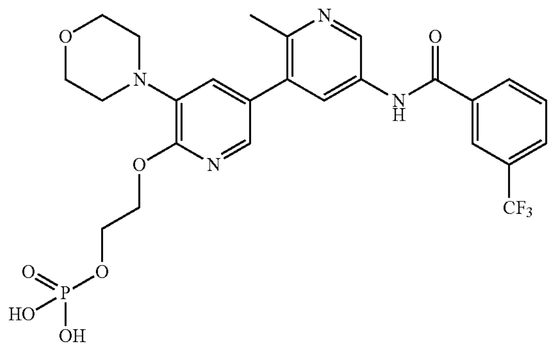 [SMILES: Cc1ncc(NC(=O)c2cccc(C(F)(F)F)c2)cc1-c1cnc(OCCOP(=O)(O)O)c(N2CCOCC2)c1] | 2-((2'-methyl-5-morpholino-5'-(3-(trifluoromethyl)benzamido)-[3,3'-bipyridin]-6-yl)oxy)ethyl dihydrogen phosphate | $^1$H NMR (400 MHz, METHANOL-d$_4$) δ ppm 2.49 (s, 3 H) 3.10-3.22 (m, 4 H) 3.78-3.90 (m, 4 H) 4.22 (q, J = 5.75 Hz, 2 H) 4.62 (t, J = 5.50 Hz, 2 H) 7.21 (d, J = 2.08 Hz, 1 H) 7.69-7.79 (m, 2 H) 7.90 (d, J = 7.83 Hz, 1 H) 8.05 (d, J = 2.45 Hz, 1 H) 8.24 (d, J = 7.82 Hz, 1 H) 8.30 (s, 1 H) 8.86 (d, J = 2.45 Hz, 1 H). LCMS (m/z) (M + H) = 583.0, Rt = 0.62 min. |

Assays

The activity of a compound according to the present invention can be assessed by well-known in vitro & in vivo methods. Raf inhibition data provided herein was obtained using the following procedures.

In Vitro Raf Activity Determination: The RAF enzymes and the catalytically inactive MEK1 protein substrate were all made in-house using conventional methods. CRAF cDNA was subcloned as full length protein, with Y340E and Y341E activating mutations, into a baculovirus expression vector for Sf9 insect cell expression. h14-3-3 zeta cDNA was subcloned into a baculovirus expression vector for SF9 insect cell expression. Sf9 cells co-expressing both proteins were lysed and subjected to immobilized nickel chromatography and eluted with Imidazole. A second column (StrepII binding column) was used and eluted with desthiobiotin. Protein Tags were removed using Prescission enzyme and the protein was further purified using a flowthrough step to remove tags.

C-Raf TR refers to a truncated C-Raf protein, a Δ1-324 deletion mutant. C-Raf FL refers to the full-length C-Raf protein.

Full length MEK1 with an inactivating K97R ATP binding site mutation is utilized as a RAF substrate. The MEK1 cDNA was subcloned with an N-terminal (his)$_6$ tag into a vector for E. Coli expression. The MEK1 substrate was purified from E. Coli lysate by nickel affinity chromatography followed by anion exchange. The final MEK1 preparation was biotinylated (Pierce EZ-Link Sulfo-NHS-LC-Biotin) and concentrated.

Assay Materials: Assay buffer is 50 mM Tris, pH 7.5, 15 mM MgCl$_2$, 0.01% Bovine Serum Albumin (BSA) and 1 mM dithiothreitol (DTT); Stop buffer is 60 mM ethylenediaminetetraacetic acid (EDTA) and 0.01% Tween® 20; b-Raf (V600E), active; biotinylated Mek, kinase dead; Alpha Screen detection kit (available from PerkinElmer™ #6760617R); Anti phospho-MEK1/2 (available from Cell Signaling Technology, Inc. #9121); 384 well low volume assay plates (White Greiner® plates).

Assay conditions: b-Raf (V600E) approximately 4 pM; c-Raf approximately 4 nM; biotinylated Mek, kinase dead approximately 10 nM; ATP 10 μM for BRAF (V600E) and 1 μM for CRAF; Pre-incubation time with compounds 60 minutes at room temperature; Reaction time 1 or 3 hours at room temperature.

Assay protocol: Raf and biotinylated Mek (kinase dead) were combined at 2× final concentrations in assay buffer (50 mM Tris, pH 7.5, 15 mM MgCl$_2$, 0.01% BSA and 1 mM DTT) and dispensed 5 ml per well in assay plates (Greiner white 384 well assay plates #781207) containing 0.25 ml of 40× of a Raf kinase inhibitor test compound diluted in 100% DMSO. The plate was incubated for 60 minutes at room temperature. The Raf kinase activity reaction was started by the addition of 5 mL per well of 2×ATP diluted in assay buffer. After 3 hours (b-Raf(V600E)) or 1 hour (c-Raf). The reactions were stopped and the phosphorylated product was measured using a rabbit anti-p-MEK (Cell Signaling, #9121) antibody and the Alpha Screen IgG (ProteinA) detection Kit (PerkinElmer #6760617R), by the addition of 10 mL to the well of a mixture of the antibody (1:2000 dilution) and detection beads (1:2000 dilution of both beads) in Stop/bead buffer (25 mM EDTA, 50 mM Tris, pH 7.5, 0.01% Tween20). The additions were carried out under dark conditions to protect the detection beads from light. A lid was placed on top of the plate and incubated for 1 hour at room temperature, after which the luminescence was read on a PerkinElmer Envision instrument. The concentration of each compound for 50% inhibition (IC$_{50}$) was calculated by non-linear regression using XL Fit data analysis software.

Solubility of the compounds of the invention was assessed in a high throughput solubility assay: compounds were received as 10 mM DMSO solutions. The DMSO stock solution was then transferred into a microtiter plate. The DMSO solvent was dried with a solvent evaporator (GeneVac). After the addition of buffer solution (pH 6.8, pH 4.0 or FaSSIF), the plate was sealed and shaken for 16-24 hours at room temperature. The plate was centrifuged for phase separation and the supernatant quantified by a RapidFire 365 High-throughput MS System (Agilant) coupled with a mass spectrometer (Sciex), using a calibration curve constructed with the same DMSO stock solution. Solubility results (μM) are obtained in triplicate.

Using the assays described above, compounds of the invention exhibit inhibitory efficacy for C-Raf and have an improved solubility profile compared to their corresponding non-phosphate molecule as detailed in table 3, below.

For example, 2-((4-(2-methyl-5-(2-(trifluoromethyl) isonicotinamido)phenyl)-6-morpholinopyridin-2-yl)oxy) ethyl dihydrogen phosphate (example 1) exhibits inhibitory efficacy of 0.1 nM for C-Raf. Further, example 1 has a solubility of 874 μM which represents a greater than 48 fold improvement compared with the corresponding non-phosphate molecule (N-(3-(2-(2-hydroxyethoxy)-6-morpholinopyridin-4-yl)-4-methylphenyl)-2-(trifluoromethyl)isonicotinamide) which has a solubility of 18 μM.

| Example | C-Raf (μM) | Solubility (non-phosphate) (μM) | Solubility (μM) |
| --- | --- | --- | --- |
| 1 | 0.0001 | 18 | 874 |
| 2 | 0.006 | 11 | <1000 |
| 3 | 0.000024 | 14 | 987 |
| 4 | 0.0007 | 31 | 617 |
| 5 | 0.0001 | 107 | 725 |
| 6 | 0.0003 | 17 | 675 |
| 7 | 0.00005 | 5 | 124 |
| 9 | 0.0005 | 17 | 841 |
| 10 | 0.0003 | 12 | 635 |
| 11 | 0.002 | 22 | <1000 |
| 12 | 0.002 | 16 | 939 |
| 13 | 0.00003 | 43 | 792 |
| 14 | 0.00004 | 177 | 897 |
| 15 | 0.0004 | 111 | 936 |
| 16 | 0.001 | 36 | <1000 |
| 17 | 0.00002 | 8 | 253 |
| 18 | 0.00002 | | |

We claim:

1. A compound of formula I:

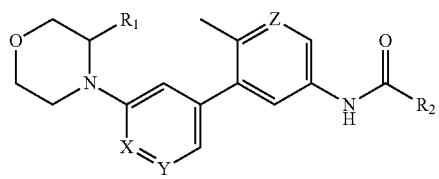

in which:

$R_1$ is selected from hydrogen and methyl;

$R_2$ is selected from pyridinyl and phenyl; wherein phenyl or pyridinyl can be substituted with a group selected from trifluoromethyl, 1,1-difluoroethyl and 2-fluoropropan-2-yl;

X and Y are independently selected from N and C—OCH$_2$CHR$_3$R$_4$; wherein R$_3$ is selected from hydrogen and OH; and R$_4$ is selected from 2-(phosphonooxy)methyl and phosphonooxy; with the proviso that if X is N, Y is C—OCH$_2$CHR$_3$R$_4$; and if Y is N, X is C—OCH$_2$CHR$_3$R$_4$; and Z is selected from N and CH; or a pharmaceutically acceptable salt thereof.

2. The compound of claim 1 of formula Ia:

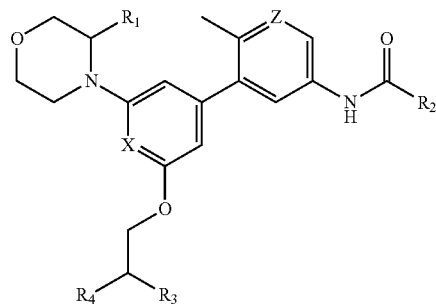

in which:

$R_1$ is selected from hydrogen and methyl;

$R_2$ is selected from pyridinyl and phenyl; wherein phenyl or pyridinyl can be substituted with a group selected from trifluoromethyl, 1,1-difluoroethyl and 2-fluoropropan-2-yl;

$R_3$ is selected from hydrogen and OH;

$R_4$ is selected from 2-(phosphonooxy)methyl and phosphonooxy; and

Z is selected from N and CH; or a pharmaceutically acceptable salt thereof.

3. The compound of claim 2, or a pharmaceutically acceptable salt thereof, selected from:

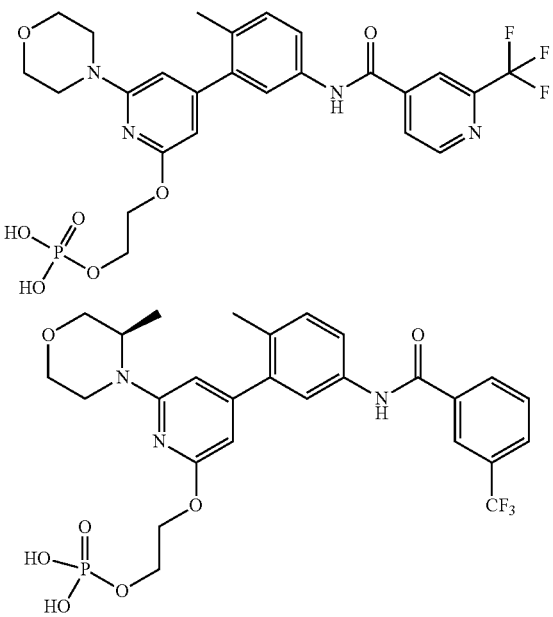

41
-continued
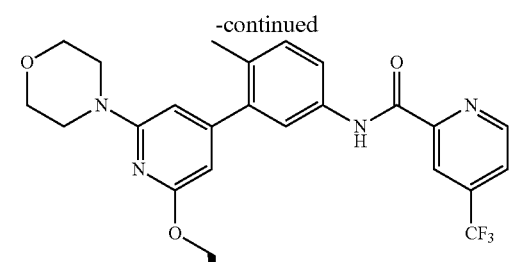
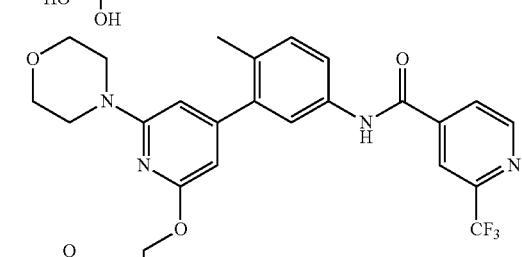
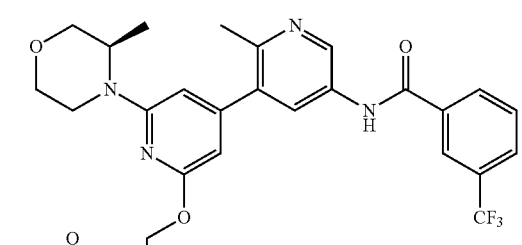
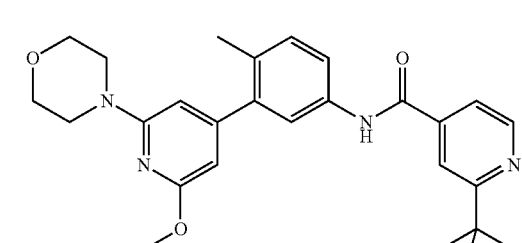
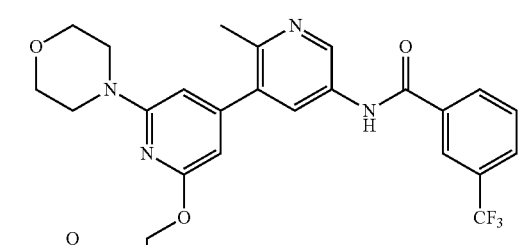
42
-continued
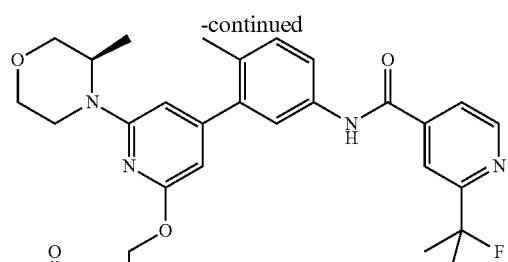
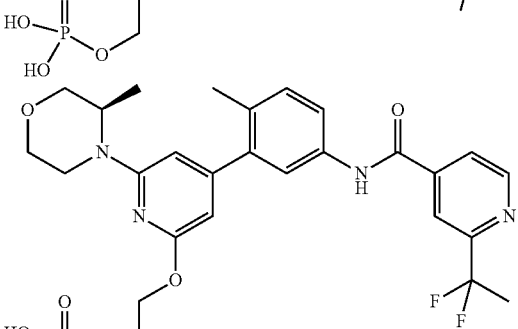
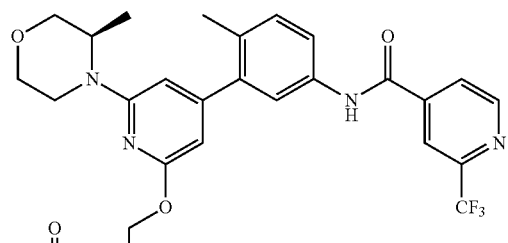
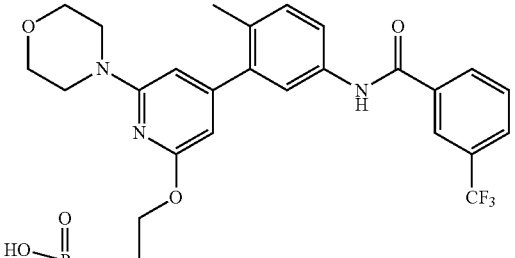
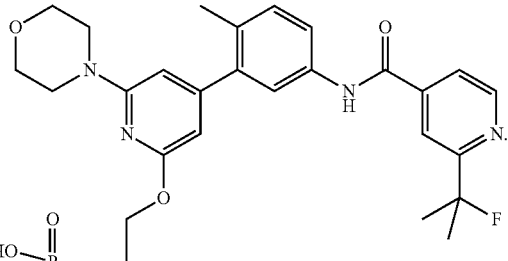

4. The compound of claim 1 of formula Ib:

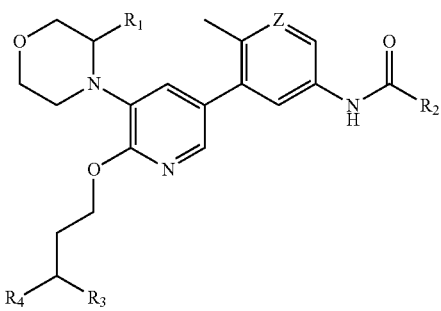

in which:
R₁ is selected from hydrogen and methyl;
R₂ is selected from pyridinyl and phenyl; wherein phenyl or pyridinyl can be substituted with a group selected from trifluoromethyl, 1,1-difluoroethyl and 2-fluoropropan-2-yl;
R₃ is selected from hydrogen and OH;
R₄ selected from 2-(phosphonooxy)methyl and phosphonooxy; and
Z is selected from N and CH; or a pharmaceutically acceptable salt thereof.

5. The compound of claim 4, or a pharmaceutically acceptable salt thereof, selected from:

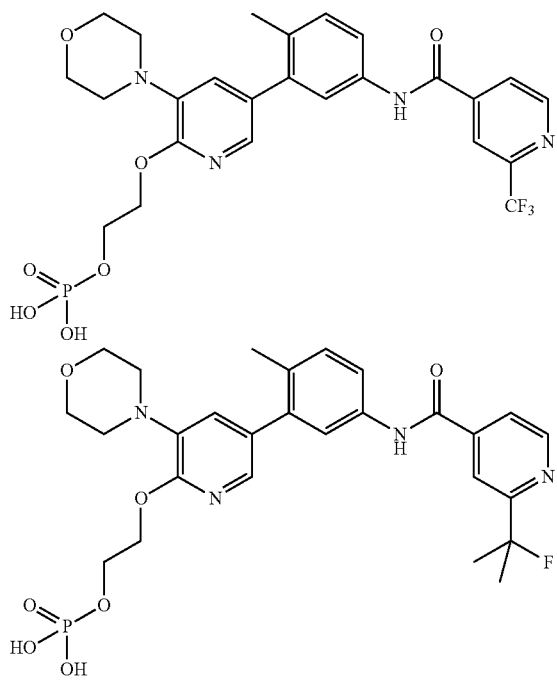

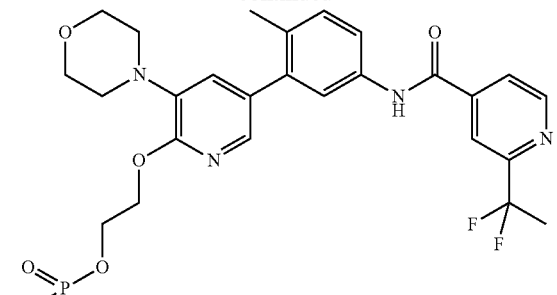

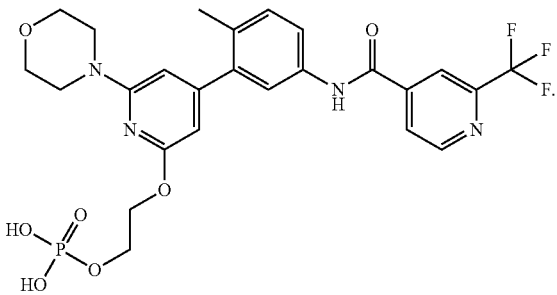 [SMILES: Cc1ccc(NC(=O)c2ccnc(C(F)(F)F)c2)cc1-c1cc(OCCOP(=O)(O)O)nc(N2CCOCC2)c1]

6. A compound, or a pharmaceutically acceptable salt thereof, of formula:

7. A pharmaceutical composition comprising a compound of claim 1 or a pharmaceutically acceptable salt thereof and one or more pharmaceutically acceptable carriers.

8. A combination comprising a therapeutically effective amount of a compound of claim 1 or a pharmaceutically acceptable salt thereof and one or more therapeutically active co-agents.

* * * * *